US010634683B2

(12) United States Patent
Eisele

(10) Patent No.: US 10,634,683 B2
(45) Date of Patent: Apr. 28, 2020

(54) METHODS FOR THE DETERMINATION OF THE BIOLOGICAL ACTIVITIES OF NEUROTOXIN POLYPEPTIDES

(71) Applicant: MERZ PHARMA GMBH & CO. KGAA, Frankfurt am Main (DE)

(72) Inventor: Karl-Heinz Eisele, Frankfurt am Main (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 186 days.

(21) Appl. No.: 15/528,219

(22) PCT Filed: Nov. 20, 2015

(86) PCT No.: PCT/EP2015/077245
§ 371 (c)(1),
(2) Date: May 19, 2017

(87) PCT Pub. No.: WO2016/079310
PCT Pub. Date: May 26, 2016

(65) Prior Publication Data
US 2018/0045733 A1    Feb. 15, 2018

(30) Foreign Application Priority Data

Nov. 21, 2014 (EP) .................................... 14194265

(51) Int. Cl.
| | | |
|---|---|---|
| C12Q 1/00 | (2006.01) | |
| G01N 33/68 | (2006.01) | |
| G01N 33/569 | (2006.01) | |
| C07K 14/705 | (2006.01) | |

(52) U.S. Cl.
CPC ... *G01N 33/6809* (2013.01); *C07K 14/70571* (2013.01); *G01N 33/56911* (2013.01); *C07K 2319/61* (2013.01)

(58) Field of Classification Search
CPC ................................................ G01N 33/6809
See application file for complete search history.

(56) References Cited

U.S. PATENT DOCUMENTS

| 8,476,068 B2 | 7/2013 | Zhu et al. |
| 2012/0122128 A1 | 5/2012 | Fernandez-Salas et al. |

FOREIGN PATENT DOCUMENTS

| WO | 2009/035476 A1 | 3/2009 |
| WO | 2010105234 A1 | 9/2010 |
| WO | 2010124998 A1 | 11/2010 |
| WO | 2013/131991 A1 | 9/2013 |
| WO | 2014/079878 A1 | 5/2014 |

OTHER PUBLICATIONS

Altschul et al., "Basic Local Alignment Search Tool", J. Mol. Biol. 1990, 215, 403-410.
Arnon et al., "Botulinum Toxin as a Biological Weapon Medical and Public Health Management", JAMA, 2001, vol. 285, No. 8, 1059-1070.
Babuska et al., "Characterization of P19 Cells during Retinoic Acid Induced Differentiation", Prague Medical Report, vol. 111, 2010, No. 4, 289-299.
Barry et al., "Introduction of Antisense Oligonucleotides into Cells by Permeabilization with Streptolysin O", Biotechniques, 1993, 15(6):1016-8.
Binz et al., "Clostridial Neurotoxins: Mechanism of SNARE Cleavage and Outlook on Potential Substrate Specificity Reengineering", Toxins, 2010, 2, 665-682.
Chen et al., "Fusion Protein Linkers: Property, Design and Functionality", Adv. Drug Deliv. Rev. 2013, 65(10):1357-1369.
Cohn et al., "Nucleotide Sequence of the luxA Gene of Vibrio harveyi and the Complete Amino Acid Sequence of the alpha Subunit of Bacterial Luciferase", J. Biol. Chem. vol. 260, No. 10, 1985, 6139-6146.
Couesnon et al., "Expression of botulinum neurotoxins A and E, and associated non-toxin genes, during the transition phase and stability at high temperature: analysis by quantitative reverse transcription-PCR", Microbiology, 2006, 152, 759-770.
Dang et al., "Prepore to pore transition of a cholesterol-dependent cytolysin visualized by electron microscopy", J. Struct. Biol. 150, 2005, 100-108.
Dressler et al., "Mouse Diaphragm Assay for Detection of Antibodies Against Botulinum Toxin Type B", Mov. Disord. 2005, 20:1617-1619.
Encinas et al., "Sequential Treatment of SH-SY5Y Cells with Retinoic Acid and Brain-Derived Neurotrophic Factor Gives Rise to Fully Differentiated, Neurotrophic Factor-Dependent, Human Neuron-Like Cells", Journal of Neurochemistry, 2000, 991-1003.

(Continued)

*Primary Examiner* — Albert M Navarro
(74) *Attorney, Agent, or Firm* — J. A. Lindeman & Co., PLLC

(57) ABSTRACT

The present invention pertains to a method for determining the biological activity of a neurotoxin, the method comprising the steps of: (a) expressing a fusion protein comprising (i) an anchor protein, (ii) a reporter protein and (iii) a neurotoxin cleavage site intervening the anchor protein and the reporter protein, in neurotoxin-sensitive cells; (b) incubating the neurotoxin-sensitive cells of (a) with a neurotoxin and cultivating the cells under conditions which allow the neurotoxin to exert its biological activity; (c) permeabilizing the neurotoxin-sensitive cells of (b) under conditions which allow the release of the reporter protein but not the release of the anchor protein from the permeabilized neurotoxin-sensitive cells; and (d) quantifying the activity of the reporter protein released from the cells, thereby determining the biological activity of the neurotoxin. In addition, the invention relates to a fusion protein comprising (i) an anchor protein, (ii) a reporter protein, and (iii) a neurotoxin cleavage site intervening the anchor protein and the reporter protein, for determining the biological activity of a neurotoxin, in neurotoxin-sensitive cells. Further encompassed by the present invention is a kit comprising the fusion protein of the invention. Finally, the invention pertains to the use of a fusion protein of the invention for determining the biological activity of a neurotoxin, in neurotoxin-sensitive cells.

14 Claims, No Drawings

Specification includes a Sequence Listing.

(56) References Cited

OTHER PUBLICATIONS

Da-Fei Feng and Russell F. Doolittle "Progressive Sequence Alignment as a Prerequisite to Correct Phylogenetic Trees", J. Mol. Evol. 1987, 25:351-360.
Fernandez-Salas et al., "Botulinum Neurotoxin Serotype a Specific Cell-Based Potency Assay to Replace the Mouse Bioassay", Plos One, 2012, vol. 7, Issue 11, e49516.
Audrey Fischer and Mauricio Montal "Single molecule detection of intermediates during botulinum neurotoxin translocation across membranes", PNAS, 2007, vol. 104, No. 25, 10447-10452.
Gailey et al., "Low-Cost System for Real-Time Monitoring of Luciferase Gene Expression", Biotechniques, 1997, 22:528-534.
Manfred Gossen and Hermann Bujard "Tight control of gene expression in mammalian cells by tetracycline-responsive promoters", Proc. Natl. Acad. Sci. 1992, vol. 89, 5547-5551.
Stephen J. Gould and Suresh Subramani "Firefly Luciferase as a Tool in Molecular and Cell Biology", Analytical Biochem. 1988, 175, 5-13.
Graves et al., "Guanine nucleotide regulation of inositol phospholipid hydrolysis and CD3-antigen phosphorylation in permeabilized T lymphocytes", J. Biochem. 1990, 265, 407-413.
Desmond G. Higgins and Paul M. Sharp "Fast and sensitive multiple sequence alignments on a microcomputer", Cabios Communication, vol. 5, No. 2, 1989, 151-153.
Johnston et al., "Nucleotide Sequence of the LuxB Gene of Vibrio harveyi and the Complete Amino Acid Sequence of the beta Subunit of Bacterial Luciferase", J. Biol. Chem. vol. 261, No. 11, 1986, 4805-4811.
Jones-Villeneuve et al., "Retinoic acid induces embryonal carcinoma cells to differentiate into neurons and glial cells", J Cell Biol. Aug. 1982; 94(2): 253-62.
Jost et al., "Botulinum Neurotoxin Type A Free of Complexing Proteins (XEOMIN) in Focal Dystonia", Drugs, 2007, 67 (5): 669-683.
Krieglstein et al., "Arrangement of disulfide bridges and positions of sulfhydryl groups in tetanus toxin", Eur. J. Biochem., (1990), 188, 39-45.
Krieglstein et al., "Limited proteolysis of tetanus toxin", Eur. J. Biochem., (1991), 202, 41-51.
Krieglstein et al., "Covalent Structure of Botulinum Neurotoxin Type A: Location of Sulfhydryl Groups, and Disulfide Bridges and Identification of C-Termini of Light and Heavy Chains", J. Protein Chem., (1994), vol. 13, No. 1, 49-57.
Lemasters, J. J. & Hackenbrock, C. R. "Kinetics of product inhibition during firefly luciferase luminescence", Biochemistry, 1977, 16(3): 445-447.
Meyer-Ficca et al., "Comparative analysis of inducible expression systems in transient transfection studies", Anal Biochem. Nov. 1, 2004; 334(1): 9-19.
Michele Migliore and Gordon M. Shepherd "An integrated approach to classifying neuronal phenotypes", Nature, 2005, 810, vol. 6, 810-818.
Saul B. Needleman and Christian D. Wunsch "A General Method Applicable to the Search for Similarities in the Amino Acid Sequence of Two Proteins", J. Mol. Bio., (1970), 48, 443-453.
Nguyen et al., "Firefly Luciferase Luminescence Assays Using Scintillation Counters for Quantitation in Transfected Mammalian Cells", Analytical Biochem. 1988, 171, 404-408.

Nielsen et al., "Expression of a preproinsulin-beta-galactosidase gene fusion in mammalian cells", (1983) Proc. Natl. Acad. Sci. 80(17): 5198-5202.
No et al., "Ecdysone-inducible gene expression in mammalian cells and transgenic mice", Proc.Natl. Acad. Sci. 1996. 93(8): 3346-3351.
Pearce et al., "Measurement of Botulinum Toxin Activity: Evaluation of the Lethality Assay", Toxicol. Appl. Pharmacol., (1994), 128, 69-77.
Pellett et al., "A neuronal cell-based botulinum neurotoxin assay for highly sensitive and specific detection of neutralizing serum antibodies", FEBS Lett. 2007, 581(25): 4803-4808.
Pellett et al., "Sensitive and quantitative detection of botulinum neurotoxin in neurons derived from mouse embryonic stem cells", Biochem. Biophys. Res. Commun. 2011, 404(1): 388-392.
Sambrook "Molecular Cloning: A Laboratory Manual", Cold Spring Harbor Laboratory, third edition, 2001.
Schiavo et al., "Neurotoxins affecting neuroexocytosis", Physiol. Rev. 2000, 80: 717-66.
Sekiya et al., "A ring-shaped structure with acrown formed by streptolysin O on the erythrocyte membrane", J Bacteriol. 1993; 175(18): 5953-61.
Seliger and McElroy "Spectral emission and quantum yield of firefly bioluminescence", Arch. Biochem. Biophys. 1960, 88:136-141.
Shockett and Schatz "Inducible gene expression using an autoregulatory, tetracycline-controlled system", Curr. Protoc. Mol. Biol. 2002, Chapter 16: Unit 16.14.
Stephen Silberstein "Botulinum Neurotoxins: Origins and Basic Mechanisms of Action", Pain Practice, 2004, vol. 4, Issue 1S, S19-S26.
Temple F. Smith "Comparison of Biosequences", Adv. Appl. Math. 2 (1981), 482-489.
Staines et al., "Retinoic acid treated P19 embryonal carcinoma cells differentiate into oligodendrocytes capable of myelination", Neuroscience. 1996, 71(3): 845-53.
Donald W. Straughan "Progress in Applying the Three Rs to the Potency Testing of Botulinum Toxin Type A", ATLA 34, (2006), 305-313.
Tilley et al., "Structural Basis of Pore Formation by the Bacterial Toxin Pneumolysin", Cell, vol. 121, 2005, 247-256.
Vieites et al., "Expression and in vivo determination of firefly luciferase as gene reporter in *Saccharomyces aerevisiae*", Yeast, 1994,10:1321-1327.
Wang et al., "A regulatory system for use in gene transfer", Proc. Natl. Acad. Sci. 1994, vol. 91, 8180-8184.
Whitemarsh et al., "Novel Application of Human Neurons Derived from Induced Pluripotent Stem Cells for Highly Sensitive Botulinum Neurotoxin Detection", Toxicol. Sci., (2012), 126(2), 426-435.
Zhou et al., "Optimization of the Tet-On system for regulated gene expression through viral evolution", Gene Ther. 2006,13(19): 1382-1390.
Zhu et al., "Tetracycline-controlled transcriptional regulation systems: advances and application in transgenic animal modeling", Semin. Cell Dev. Biol. 2002, 13:121-8.
International Search Report and Written Opinion in International Application No. PCT/EP2015/077245, dated Feb. 11, 2016.
Dong et al., "Using fluorescent sensors to detect botulinum neurotoxin activity in vitro and in living cells," PNAS, Jan. 1, 2004, vol. 101, No. 41, pp. 14701-14706.
Regan Fulton and Brian Van Ness "Luminescent Reported Gene Assays for Luciferase and beta-Galactosidase Using a Liquid Scintillation Counter", Biotechniques, 1993, 14:762-763.

SEQUENCE LISTING

```
<160> NUMBER OF SEQ ID NOS: 5

<210> SEQ ID NO 1
<211> LENGTH: 4722
<212> TYPE: DNA
<213> ORGANISM: Artificial
<220> FEATURE:
<223> OTHER INFORMATION: CHT-GFP-SNAP-LUC

<400> SEQUENCE: 1
atggctttcc atgtggaagg actgatagct atcatcgtgt tctaccttct aattttgctg      60
gttggaatat gggctgcctg gagaaccaaa aacagtggca gcgcagaaga gcgcagcgaa     120
gccatcatag ttggtggccg agatattggt ttattggttg gtggatttac catgacagct     180
acctgggtcg gaggagggta tatcaatggc acagctgaag cagtttatgt accaggttat     240
ggcctagctt gggctcaggc accaattgga tattctctta gtctgatttt aggtggcctg     300
ttctttgcaa aacctatgcg ttcaaagggg tatgtgacca tgttagaccc gtttcagcaa     360
atctatggaa aacgcatggg cggactcctg tttattcctg cactgatggg agaaatgttc     420
```

```
tgggctgcag caattttctc tgctttggga gccaccatca gcgtgatcat cgatgtggat    480
atgcacattt ctgtcatcat ctctgcactc attgccactc tgtacacact ggtgggaggg    540
ctctattctg tggcctacac tgatgtcgtt cagctctttt gcattttgt agggctgtgg     600 atcagcgtcc cctttgcatt gtcacatcct gcagtcgcag acatcgggtt cactgctgtg    660
catgccaaat accaaaagcc gtggctggga actgttgact catctgaagt ctactcttgg    720
cttgatagtt ttctgttgtt gatgctgggt ggaatcccat ggcaagcata ctttcagagg    780
gttctctctt cttcctcagc cacctatgct caagtgctgt ccttcctggc agctttcggg    840
tgcctggtga tggccatccc agccatactc attggggcca ttggagcatc aacagactgg    900
aaccagactg catatgggct tccagatccc aagactacag aagaggcaga catgattta     960 ccaattgttc tgcagtatct ctgccctgtg tatatttctt tctttggtct tggtgcagtt   1020
tctgctgctg ttatgtcatc agcagattct tccatcttgt cagcaagttc catgtttgca   1080
cggaacatct accagctttc cttcagacaa aatgcttcgg acaaagaaat cgtttgggtt   1140
atgcgaatca cagtgtttgt gtttggagca tctgcaacag ccatggcctt gctgacgaaa   1200
actgtgtatg ggctctggta cctcagttct gaccttgttt acatcgttat cttccccag    1260 ctgctttgtg tactctttgt taagggaacc aacacctatg gggccgtggc aggttatgtt   1320
tctggcctct tcctgagaat aactggaggg gagccatatc tgtatcttca gcccttgatc   1380
ttctaccctg gctattaccc tgatgataat ggtatatata atcagaaatt tccatttaaa   1440
acacttgcca tggttacatc attcttaacc aacatttgca tctcctatct agccaagtat   1500
ctatttgaaa gtggaacctt gccacctaaa ttagatgtat tgatgctgt tgttgcaaga    1560 cacagtgaag aaaacatgga taagacaatt cttgtcaaaa atgaaaatat taaattagat   1620
gaacttgcac ttgtgaagcc acgacagagc atgaccctca gctcaacttt caccaataaa   1680
gaggccttcc ttgatgttga ttccagtcca gaagggtctg ggactgaaga taatttacag   1740
atgagtaaag gagaagaact tttcactgga gttgtcccaa ttcttgttga attagatggt   1800
gatgttaatg gcacaaaatt ttctgtcagt ggagagggtg aaggtgatgc aacatacgga   1860
aaacttaccc ttaaatttat ttgcactact ggaaaactac ctgttccatg gccaacactt   1920
gtcactactt tctcttatgg tgttcaatgc ttttcaagat acccagatca tatgaaacag   1980
catgactttt tcaagagtgc catgcccgaa ggttatgtac aggaaagaac tatattttc    2040 aaagatgacg ggaactacaa gacacgtgct gaagtcaagt ttgaaggtga taccttgtt   2100 aatagaatcg agttaaaagg tattgatttt aaagaagatg gaacattct ggacacaaa    2160 ttggaataca actataactc acacaatgta tacatcatgg cagacaaaca aaagaatgga   2220
atcaaagtta acttcaaaat tagacacaac attgaagatg gaagcgttca actagcagac   2280
cattatcaac aaaatactcc aattggcgat ggccctgtcc ttttaccaga caaccattac   2340
ctgtccacac aatctgccct ttcgaaagat cccaacgaaa agagagacca catggtcctt   2400
cttgagtttg taacagctgc tgggattaca catggcatgg atgaactata caaaatggcc   2460
gaagacgcag acatgcgcaa tgagctggag agatgcagc aagggctga ccagttggct    2520 gatgagtcgt ggaaagcac ccgtcgtatg ctgcaactgg ttgaagagag taaagatgct   2580
ggtatcagga cttttggtta tgttggatgaa caaggagaac aactggaacg cattgaggaa   2640
gggatggacc aaatcaataa ggacatgaaa gaagcagaaa gaatttgac ggacctagga   2700 aaattctgcg gctttgtgt gtgtccctgt aacaagctta atcaagtga tgcttacaaa   2760 aaagcctggg gcaataatca ggacggagtg gtggccagcc agcctgctcg tgtagtggac   2820
```

-continued

```
gaacgggagc agatggccat cagtggcggc ttcatccgca gggtaacaaa tgatgcccga    2880
gaaaatgaaa tggatgaaaa cctagagcag gtgagcggca tcatcgggaa cctccgtcac    2940
atggccctgg atatgggcaa tgagatcgat acacagaatc gccagatcga caggatcatg    3000
gagaaggctg attccaacaa aaccagaatt gatgaggcca accaacgtgc aacaaagatg    3060
ctgggaagtg gtatggaaga cgccaaaaac ataagaaag gcccggcgcc attctatcct    3120
ctagaggatg aaccgctgg agagcaactg cataaggcta tgaagagata cgccctggtt    3180
cctggaacaa ttgcttttac agatgcacat atcgaggtga acatcacgta cgcggaatac    3240
ttcgaaatgt ccgttcggtt ggcagaagct atgaaacgat atgggctgaa tacaaatcac    3300
agaatcgtcg tatgcagtga aaactctctt caattcttta tgccggtgtt gggcgcgtta    3360
tttatcggag ttgcagttgc gcccgcgaac gacatttata tgaacgtga attgctcaac    3420 agtatgaaca tttcgcagcc taccgtagtg tttgtttcca aaaggggtt gcaaaaaatt    3480 ttgaacgtgc aaaaaaatt accaataatc cagaaaatta ttatcatgga ttctaaaacg    3540
gattaccagg gatttcagtc gatgtacacg ttcgtcacat ctcatctacc tcccggtttt    3600
aatgaatacg attttgtacc agagtccttt gatcgtgaca aaacaattgc actgataatg    3660
aattcctctg gatctactgg gttacctaag ggtgtggccc ttccgcatag aactgcctgc    3720
gtcagattct cgcatgccag agatcctatt tttggcaatc aaatcattcc ggatactgcg    3780
attttaagtg ttgttccatt ccatcacggt tttggaatgt ttactacact cggatatttg    3840
atatgtggat ttcgagtcgt cttaatgtat agatttgaag aagagctgtt tttacgatcc    3900
cttcaggatt acaaaattca aagtgcgttg ctagtaccaa ccctattttc attcttcgcc    3960
aaaagcactc tgattgacaa atacgattta tctaatttac acgaaattgc ttctggggc    4020 gcacctcttt cgaaagaagt cggggaagcg gttgcaaaac gcttccatct tccagggata    4080
cgacaaggat atgggctcac tgagactaca tcagctattc tgattacacc cgaggggat    4140 gataaaccgg gcgcggtcgg taaagttgtt ccattttttg aagcgaaggt tgtggatctg    4200
gataccggga aaacgctggg cgttaatcag agaggcgaat tatgtgtcag aggacctatg    4260
attatgtccg gttatgtaaa caatccggaa gcgaccaacg ccttgattga caaggatgga    4320
tggctacatt ctggagacat agcttactgg gacgaagacg aacacttctt catagttgac    4380
cgcttgaagt ctttaattaa atacaaagga tatcaggtgg ccccgctga attggaatcg    4440 atattgttac aacaccccaa catcttcgac gcgggcgtgg caggtcttcc cgacgatgac    4500
gccggtgaac ttcccgccgc cgttgttgtt ttggagcacg aaagacgat gacgaaaaa    4560 gagatcgtgg attacgtcgc cagtcaagta caaccgcga aaagttgcg cggaggagtt    4620 gtgtttgtgg acgaagtacc gaaaggtctt accggaaaac tcgacgcaag aaaaatcaga    4680
gagatcctca taaaggccaa gaagggcgga aagtccaaat tg    4722
```

<210> SEQ ID NO 2
<211> LENGTH: 1574
<212> TYPE: PRT
<213> ORGANISM: Artificial
<220> FEATURE:
<223> OTHER INFORMATION: fusion protein

<400> SEQUENCE: 2

```
Met Ala Phe His Val Glu Gly Leu Ile Ala Ile Ile Val Phe Tyr Leu
1               5                   10                  15

Leu Ile Leu Leu Val Gly Ile Trp Ala Ala Trp Arg Thr Lys Asn Ser
```

```
                20                  25                  30
Gly Ser Ala Glu Glu Arg Ser Glu Ala Ile Ile Val Gly Gly Arg Asp
            35                  40                  45
Ile Gly Leu Leu Val Gly Gly Phe Thr Met Thr Ala Thr Trp Val Gly
50                  55                  60
Gly Gly Tyr Ile Asn Gly Thr Ala Glu Ala Val Tyr Val Pro Gly Tyr
65                  70                  75                  80
Gly Leu Ala Trp Ala Gln Ala Pro Ile Gly Tyr Ser Leu Ser Leu Ile
                85                  90                  95
Leu Gly Gly Leu Phe Phe Ala Lys Pro Met Arg Ser Lys Gly Tyr Val
            100                 105                 110
Thr Met Leu Asp Pro Phe Gln Gln Ile Tyr Gly Lys Arg Met Gly Gly
            115                 120                 125
Leu Leu Phe Ile Pro Ala Leu Met Gly Glu Met Phe Trp Ala Ala Ala
            130                 135                 140
Ile Phe Ser Ala Leu Gly Ala Thr Ile Ser Val Ile Ile Asp Val Asp
145                 150                 155                 160
Met His Ile Ser Val Ile Ile Ser Ala Leu Ile Ala Thr Leu Tyr Thr
                165                 170                 175
Leu Val Gly Gly Leu Tyr Ser Val Ala Tyr Thr Asp Val Val Gln Leu
            180                 185                 190
Phe Cys Ile Phe Val Gly Leu Trp Ile Ser Val Pro Phe Ala Leu Ser
            195                 200                 205
His Pro Ala Val Ala Asp Ile Gly Phe Thr Ala Val His Ala Lys Tyr
            210                 215                 220
Gln Lys Pro Trp Leu Gly Thr Val Asp Ser Ser Glu Val Tyr Ser Trp
225                 230                 235                 240
Leu Asp Ser Phe Leu Leu Leu Met Leu Gly Gly Ile Pro Trp Gln Ala
                245                 250                 255
Tyr Phe Gln Arg Val Leu Ser Ser Ser Ala Thr Tyr Ala Gln Val
            260                 265                 270
Leu Ser Phe Leu Ala Ala Phe Gly Cys Leu Val Met Ala Ile Pro Ala
            275                 280                 285
Ile Leu Ile Gly Ala Ile Gly Ala Ser Thr Asp Trp Asn Gln Thr Ala
            290                 295                 300
Tyr Gly Leu Pro Asp Pro Lys Thr Thr Glu Glu Ala Asp Met Ile Leu
305                 310                 315                 320
Pro Ile Val Leu Gln Tyr Leu Cys Pro Val Tyr Ile Ser Phe Phe Gly
                325                 330                 335
Leu Gly Ala Val Ser Ala Ala Val Met Ser Ser Ala Asp Ser Ser Ile
            340                 345                 350
Leu Ser Ala Ser Ser Met Phe Ala Arg Asn Ile Tyr Gln Leu Ser Phe
            355                 360                 365
Arg Gln Asn Ala Ser Asp Lys Glu Ile Val Trp Val Met Arg Ile Thr
            370                 375                 380
Val Phe Val Phe Gly Ala Ser Ala Thr Ala Met Ala Leu Leu Thr Lys
385                 390                 395                 400
Thr Val Tyr Gly Leu Trp Tyr Leu Ser Ser Asp Leu Val Tyr Ile Val
                405                 410                 415
Ile Phe Pro Gln Leu Leu Cys Val Leu Phe Val Lys Gly Thr Asn Thr
            420                 425                 430
Tyr Gly Ala Val Ala Gly Tyr Val Ser Gly Leu Phe Leu Arg Ile Thr
            435                 440                 445
```

```
Gly Gly Glu Pro Tyr Leu Tyr Leu Gln Pro Leu Ile Phe Tyr Pro Gly
            450                 455                 460

Tyr Tyr Pro Asp Asp Asn Gly Ile Tyr Asn Gln Lys Phe Pro Phe Lys
465                 470                 475                 480

Thr Leu Ala Met Val Thr Ser Phe Leu Thr Asn Ile Cys Ile Ser Tyr
                        485                 490                 495

Leu Ala Lys Tyr Leu Phe Glu Ser Gly Thr Leu Pro Pro Lys Leu Asp
            500                 505                 510

Val Phe Asp Ala Val Val Ala Arg His Ser Glu Glu Asn Met Asp Lys
            515                 520                 525

Thr Ile Leu Val Lys Asn Glu Asn Ile Lys Leu Asp Glu Leu Ala Leu
            530                 535                 540

Val Lys Pro Arg Gln Ser Met Thr Leu Ser Ser Thr Phe Thr Asn Lys
545                 550                 555                 560

Glu Ala Phe Leu Asp Val Asp Ser Ser Pro Glu Gly Ser Gly Thr Glu
            565                 570                 575

Asp Asn Leu Gln Met Ser Lys Gly Glu Glu Leu Phe Thr Gly Val Val
            580                 585                 590

Pro Ile Leu Val Glu Leu Asp Gly Asp Val Asn Gly His Lys Phe Ser
            595                 600                 605

Val Ser Gly Glu Gly Glu Gly Asp Ala Thr Tyr Gly Lys Leu Thr Leu
            610                 615                 620

Lys Phe Ile Cys Thr Thr Gly Lys Leu Pro Val Pro Trp Pro Thr Leu
625                 630                 635                 640

Val Thr Thr Phe Ser Tyr Gly Val Gln Cys Phe Ser Arg Tyr Pro Asp
                        645                 650                 655

His Met Lys Gln His Asp Phe Phe Lys Ser Ala Met Pro Glu Gly Tyr
                660                 665                 670

Val Gln Glu Arg Thr Ile Phe Phe Lys Asp Asp Gly Asn Tyr Lys Thr
            675                 680                 685

Arg Ala Glu Val Lys Phe Glu Gly Asp Thr Leu Val Asn Arg Ile Glu
            690                 695                 700

Leu Lys Gly Ile Asp Phe Lys Glu Asp Gly Asn Ile Leu Gly His Lys
705                 710                 715                 720

Leu Glu Tyr Asn Tyr Asn Ser His Asn Val Tyr Ile Met Ala Asp Lys
                        725                 730                 735

Gln Lys Asn Gly Ile Lys Val Asn Phe Lys Ile Arg His Asn Ile Glu
            740                 745                 750

Asp Gly Ser Val Gln Leu Ala Asp His Tyr Gln Gln Asn Thr Pro Ile
            755                 760                 765

Gly Asp Gly Pro Val Leu Leu Pro Asp Asn His Tyr Leu Ser Thr Gln
770                 775                 780

Ser Ala Leu Ser Lys Asp Pro Asn Glu Lys Arg Asp His Met Val Leu
785                 790                 795                 800

Leu Glu Phe Val Thr Ala Ala Gly Ile Thr His Gly Met Asp Glu Leu
                        805                 810                 815

Tyr Lys Met Ala Glu Asp Ala Asp Met Arg Asn Glu Leu Glu Glu Met
            820                 825                 830

Gln Arg Arg Ala Asp Gln Leu Ala Asp Glu Ser Leu Glu Ser Thr Arg
            835                 840                 845

Arg Met Leu Gln Leu Val Glu Glu Ser Lys Asp Ala Gly Ile Arg Thr
850                 855                 860
```

```
Leu Val Met Leu Asp Glu Gln Gly Glu Gln Leu Glu Arg Ile Glu
865                 870                 875                 880

Gly Met Asp Gln Ile Asn Lys Asp Met Lys Glu Ala Glu Lys Asn Leu
            885                 890                 895

Thr Asp Leu Gly Lys Phe Cys Gly Leu Cys Val Cys Pro Cys Asn Lys
            900                 905                 910

Leu Lys Ser Ser Asp Ala Tyr Lys Lys Ala Trp Gly Asn Asn Gln Asp
            915                 920                 925

Gly Val Val Ala Ser Gln Pro Ala Arg Val Val Asp Glu Arg Glu Gln
            930                 935                 940

Met Ala Ile Ser Gly Gly Phe Ile Arg Arg Val Thr Asn Asp Ala Arg
945                 950                 955                 960

Glu Asn Glu Met Asp Glu Asn Leu Glu Gln Val Ser Gly Ile Ile Gly
                965                 970                 975

Asn Leu Arg His Met Ala Leu Asp Met Gly Asn Glu Ile Asp Thr Gln
            980                 985                 990

Asn Arg Gln Ile Asp Arg Ile Met Glu Lys Ala Asp Ser Asn Lys Thr
            995                 1000                1005

Arg Ile Asp Glu Ala Asn Gln Arg Ala Thr Lys Met Leu Gly Ser
        1010                1015                1020

Gly Met Glu Asp Ala Lys Asn Ile Lys Lys Gly Pro Ala Pro Phe
        1025                1030                1035

Tyr Pro Leu Glu Asp Gly Thr Ala Gly Glu Gln Leu His Lys Ala
        1040                1045                1050

Met Lys Arg Tyr Ala Leu Val Pro Gly Thr Ile Ala Phe Thr Asp
        1055                1060                1065

Ala His Ile Glu Val Asn Ile Thr Tyr Ala Glu Tyr Phe Glu Met
        1070                1075                1080

Ser Val Arg Leu Ala Glu Ala Met Lys Arg Tyr Gly Leu Asn Thr
        1085                1090                1095

Asn His Arg Ile Val Val Cys Ser Glu Asn Ser Leu Gln Phe Phe
        1100                1105                1110

Met Pro Val Leu Gly Ala Leu Phe Ile Gly Val Ala Val Ala Pro
        1115                1120                1125

Ala Asn Asp Ile Tyr Asn Glu Arg Glu Leu Leu Asn Ser Met Asn
        1130                1135                1140

Ile Ser Gln Pro Thr Val Val Phe Val Ser Lys Lys Gly Leu Gln
        1145                1150                1155

Lys Ile Leu Asn Val Gln Lys Lys Leu Pro Ile Ile Gln Lys Ile
        1160                1165                1170

Ile Ile Met Asp Ser Lys Thr Asp Tyr Gln Gly Phe Gln Ser Met
        1175                1180                1185

Tyr Thr Phe Val Thr Ser His Leu Pro Pro Gly Phe Asn Glu Tyr
        1190                1195                1200

Asp Phe Val Pro Glu Ser Phe Asp Arg Asp Lys Thr Ile Ala Leu
        1205                1210                1215

Ile Met Asn Ser Ser Gly Ser Thr Gly Leu Pro Lys Gly Val Ala
        1220                1225                1230

Leu Pro His Arg Thr Ala Cys Val Arg Phe Ser His Ala Arg Asp
        1235                1240                1245

Pro Ile Phe Gly Asn Gln Ile Ile Pro Asp Thr Ala Ile Leu Ser
        1250                1255                1260

Val Val Pro Phe His His Gly Phe Gly Met Phe Thr Thr Leu Gly
```

Tyr Leu Ile Cys Gly Phe Arg Val Val Leu Met Tyr Arg Phe Glu
            1265                1270                1275

Glu Glu Leu Phe Leu Arg Ser Leu Gln Asp Tyr Lys Ile Gln Ser
        1280                1285                1290

Ala Leu Leu Val Pro Thr Leu Phe Ser Phe Phe Ala Lys Ser Thr
    1295                1300                1305

Leu Ile Asp Lys Tyr Asp Leu Ser Asn Leu His Glu Ile Ala Ser
1310                1315                1320

Gly Gly Ala Pro Leu Ser Lys Glu Val Gly Glu Ala Val Ala Lys
        1325                1330                1335

Arg Phe His Leu Pro Gly Ile Arg Gln Gly Tyr Gly Leu Thr Glu
    1340                1345                1350

Thr Thr Ser Ala Ile Leu Ile Thr Pro Glu Gly Asp Asp Lys Pro
1355                1360                1365

Gly Ala Val Gly Lys Val Val Pro Phe Phe Glu Ala Lys Val Val
        1370                1375                1380

Asp Leu Asp Thr Gly Lys Thr Leu Gly Val Asn Gln Arg Gly Glu
    1385                1390                1395

Leu Cys Val Arg Gly Pro Met Ile Met Ser Gly Tyr Val Asn Asn
1400                1405                1410

Pro Glu Ala Thr Asn Ala Leu Ile Asp Lys Asp Gly Trp Leu His
        1415                1420                1425

Ser Gly Asp Ile Ala Tyr Trp Asp Glu Asp Glu His Phe Phe Ile
    1430                1435                1440

Val Asp Arg Leu Lys Ser Leu Ile Lys Tyr Lys Gly Tyr Gln Val
1445                1450                1455

Ala Pro Ala Glu Leu Glu Ser Ile Leu Leu Gln His Pro Asn Ile
        1460                1465                1470

Phe Asp Ala Gly Val Ala Gly Leu Pro Asp Asp Asp Ala Gly Glu
    1475                1480                1485

Leu Pro Ala Ala Val Val Val Leu Glu His Gly Lys Thr Met Thr
1490                1495                1500

Glu Lys Glu Ile Val Asp Tyr Val Ala Ser Gln Val Thr Thr Ala
        1505                1510                1515

Lys Lys Leu Arg Gly Gly Val Val Phe Val Asp Glu Val Pro Lys
    1520                1525                1530

Gly Leu Thr Gly Lys Leu Asp Ala Arg Lys Ile Arg Glu Ile Leu
1535                1540                1545

Ile Lys Ala Lys Lys Gly Gly Lys Ser Lys Leu
        1550                1555

<210> SEQ ID NO 3
<211> LENGTH: 3729
<212> TYPE: DNA
<213> ORGANISM: Artificial
<220> FEATURE:
<223> OTHER INFORMATION: H1R-SNAP-Luc

<400> SEQUENCE: 3
atgagcctcc ccaattcctc ctgcctctta gaagacaaga tgtgtgaggg caacaagacc      60
actatggcca gccccagct gatgcccctg gtggtggtcc tgagcactat ctgcttggtc     120
acagtagggc tcaacctgct ggtgctgtat gccgtacgga gtgagcggaa gctccacact     180
gtggggaacc tgtacatcgt cagcctctcg gtggcggact tgatcgtggg tgccgtcgtc     240

| | |
|---|---|
| atgcctatga acatcctcta cctgctcatg tccaagtggt cactgggccg tcctctctgc | 300 |
| ctcttttggc tttccatgga ctatgtggcc agcacagcgt ccattttcag tgtcttcatc | 360 |
| ctgtgcattg atcgctaccg ctctgtccag cagcccctca ggtaccttaa gtatcgtacc | 420 |
| aagacccgag cctcggccac cattctgggg gcctggtttc tctcttttct gtgggttatt | 480 |
| cccattctag gctggaatca cttcatgcag cagacctcgg tgcgccgaga ggacaagtgt | 540 |
| gagacagact tctatgatgt cacctggttc aaggtcatga ctgccatcat caacttctac | 600 |
| ctgcccacct tgctcatgct ctggttctat gccaagatct acaaggccgt acgacaacac | 660 |
| tgccagcacc gggagctcat caataggtcc ctcccttcct tctcagaaat taagctgagg | 720 |
| ccagagaacc ccaaggggga tgccaagaaa cagggaagg agtctccctg ggaggttctg | 780 |
| aaaaggaagc caaagatgc tggtggtgga tctgtcttga agtcaccatc ccaaccccc | 840 |
| aaggagatga atccccagt tgtcttcagc caagaggatg atagagaagt agacaaactc | 900 |
| tactgctttc cacttgatat tgtgcacatg caggctgcgg cagaggggag tagcagggac | 960 |
| tatgtagccg tcaaccggag ccatggccag ctcaagacag atgagcaggg cctgaacaca | 1020 |
| catggggcca gcgagatatc agaggatcag atgttaggtg atagccaatc cttctctcga | 1080 |
| acggactcag ataccaccac agagacagca ccaggcaaag gcaaattgag gagtgggtct | 1140 |
| aacacaggcc tggattacat caagtttact tggaagaggc tccgctcgca ttcaagacag | 1200 |
| tatgtatctg ggttgcacat gaaccgcgaa aggaaggccg ccaaacagtt gggtttatc | 1260 |
| atggcagcct tcatcctctg ctggatccct tatttcatct tcttcatggt cattgccttc | 1320 |
| tgcaagaact gttgcaatga acatttgcac atgttcacca tctggctggg ctacatcaac | 1380 |
| tccacactga acccctcat ctacccttg tgcaatgaga acttcaagaa gacattcaag | 1440 |
| agaattctgc atattcgctc catggccgaa gacgcagaca tgcgcaatga gctggaggag | 1500 |
| atgcagcgaa gggctgacca gttggctgat gagtcgctgg aaagcacccg tcgtatgctg | 1560 |
| caactggttg aagagagtaa agatgctggt atcaggactt tggttatgtt ggatgaacaa | 1620 |
| ggagaacaac tggaacgcat tgaggaaggg atggaccaaa tcaataagga catgaaagaa | 1680 |
| gcagaaaaga atttgacgga cctaggaaaa ttctgcgggc tttgtgtgtg tccctgtaac | 1740 |
| aagcttaaat caagtgatgc ttacaaaaaa gcctggggca ataatcagga cggagtggtg | 1800 |
| gccagccagc ctgctcgtgt agtggacgaa cgggagcaga tggccatcag tggcggcttc | 1860 |
| atccgcaggg taacaaatga tgcccgagaa aatgaaatgg atgaaaacct agagcaggtg | 1920 |
| agcggcatca tcgggaacct ccgtcacatg gccctggata tgggcaatga gatcgataca | 1980 |
| cagaatcgcc agatcgacag gatcatggag aaggctgatt ccaacaaaac cagaattgat | 2040 |
| gaggccaacc aacgtgcaac aaagatgctg ggaagtggta tggaagacgc caaaaacata | 2100 |
| aagaaaggcc cggcgccatt ctatcctcta gaggatggaa ccgctggaga gcaactgcat | 2160 |
| aaggctatga gagatacgc cctggttcct ggaacaattg cttttacaga tgcacatatc | 2220 |
| gaggtgaaca tcacgtacgc ggaatacttc gaaatgtccg ttcggttggc agaagctatg | 2280 |
| aaacgatatg gctgaatac aaatcacaga atcgtcgtat gcagtgaaaa ctctcttcaa | 2340 |
| ttctttatgc cggtgttggg cgcgttattt atcgagttg cagttgcgcc cgcgaacgac | 2400 |
| atttataatg aacgtgaatt gctcaacagt atgaacattt cgcagcctac cgtagtgttt | 2460 |
| gtttccaaaa aggggttgca aaaattttg aacgtgcaaa aaaattacc aataatccag | 2520 |
| aaaattatta tcatggattc taaaacggat taccagggat ttcagtcgat gtacacgttc | 2580 |

```
gtcacatctc atctacctcc cggttttaat gaatacgatt ttgtaccaga gtcctttgat    2640
cgtgacaaaa caattgcact gataatgaat tcctctggat ctactgggtt acctaagggt    2700
gtggcccttc cgcatagaac tgcctgcgtc agattctcgc atgccagaga tcctattttt    2760
ggcaatcaaa tcattccgga tactgcgatt ttaagtgttg ttccattcca tcacggtttt    2820
ggaatgttta ctacactcgg atatttgata tgtggatttc gagtcgtctt aatgtataga    2880
tttgaagaag agctgttttt acgatccctt caggattaca aaattcaaag tgcgttgcta    2940
gtaccaaccc tattttcatt cttcgccaaa agcactctga ttgacaaata cgatttatct    3000
aatttacacg aaattgcttc tggggggcgca cctctttcga agaagtcgg ggaagcggtt    3060 gcaaaacgct tccatcttcc agggatacga caaggatatg gctcactga gactacatca    3120 gctattctga ttacacccga gggggatgat aaaccgggcg cggtcggtaa agttgttcca    3180 tttttgaag cgaaggttgt ggatctggat accgggaaaa cgctgggcgt taatcagaga    3240
ggcgaattat gtgtcagagg acctatgatt atgtccggtt atgtaaacaa tccggaagcg    3300
accaacgcct tgattgacaa ggatggatgg ctacattctg agacatagc ttactgggac    3360 gaagacgaac acttcttcat agttgaccgc ttgaagtctt taattaaata caaaggatat    3420
caggtggccc ccgctgaatt ggaatcgata ttgttacaac accccaacat cttcgacgcg    3480
ggcgtggcag gtcttcccga cgatgacgcc ggtgaacttc ccgccgccgt tgttgttttg    3540
gagcacggaa agacgatgac ggaaaaagag atcgtggatt acgtcgccag tcaagtaaca    3600
accgcgaaaa agttgcgcgg aggagttgtg tttgtggacg aagtaccgaa aggtcttacc    3660
ggaaaactcg acgcaagaaa aatcagagag atcctcataa aggccaagaa gggcggaaag    3720
tccaaattg                                                            3729
```

```
<210> SEQ ID NO 4
<211> LENGTH: 1243
<212> TYPE: PRT
<213> ORGANISM: Artificial
<220> FEATURE:
<223> OTHER INFORMATION: fusion protein

<400> SEQUENCE: 4
```

```
Met Ser Leu Pro Asn Ser Ser Cys Leu Leu Glu Asp Lys Met Cys Glu
1               5                   10                  15

Gly Asn Lys Thr Thr Met Ala Ser Pro Gln Leu Met Pro Leu Val Val
            20                  25                  30

Val Leu Ser Thr Ile Cys Leu Val Thr Val Gly Leu Asn Leu Leu Val
        35                  40                  45

Leu Tyr Ala Val Arg Ser Glu Arg Lys Leu His Thr Val Gly Asn Leu
    50                  55                  60

Tyr Ile Val Ser Leu Ser Val Ala Asp Leu Ile Val Gly Ala Val Val
65                  70                  75                  80

Met Pro Met Asn Ile Leu Tyr Leu Leu Met Ser Lys Trp Ser Leu Gly
                85                  90                  95

Arg Pro Leu Cys Leu Phe Trp Leu Ser Met Asp Tyr Val Ala Ser Thr
            100                 105                 110

Ala Ser Ile Phe Ser Val Phe Ile Leu Cys Ile Asp Arg Tyr Arg Ser
        115                 120                 125

Val Gln Gln Pro Leu Arg Tyr Leu Lys Tyr Arg Thr Lys Thr Arg Ala
    130                 135                 140

Ser Ala Thr Ile Leu Gly Ala Trp Phe Leu Ser Phe Leu Trp Val Ile
145                 150                 155                 160
```

```
Pro Ile Leu Gly Trp Asn His Phe Met Gln Gln Thr Ser Val Arg Arg
                165                 170                 175

Glu Asp Lys Cys Glu Thr Asp Phe Tyr Asp Val Thr Trp Phe Lys Val
            180                 185                 190

Met Thr Ala Ile Ile Asn Phe Tyr Leu Pro Thr Leu Leu Met Leu Trp
        195                 200                 205

Phe Tyr Ala Lys Ile Tyr Lys Ala Val Arg Gln His Cys Gln His Arg
    210                 215                 220

Glu Leu Ile Asn Arg Ser Leu Pro Ser Phe Ser Glu Ile Lys Leu Arg
225                 230                 235                 240

Pro Glu Asn Pro Lys Gly Asp Ala Lys Lys Pro Gly Lys Glu Ser Pro
                245                 250                 255

Trp Glu Val Leu Lys Arg Lys Pro Lys Asp Ala Gly Gly Gly Ser Val
            260                 265                 270

Leu Lys Ser Pro Ser Gln Thr Pro Lys Glu Met Lys Ser Pro Val Val
        275                 280                 285

Phe Ser Gln Glu Asp Asp Arg Glu Val Asp Lys Leu Tyr Cys Phe Pro
    290                 295                 300

Leu Asp Ile Val His Met Gln Ala Ala Ala Glu Gly Ser Ser Arg Asp
305                 310                 315                 320

Tyr Val Ala Val Asn Arg Ser His Gly Gln Leu Lys Thr Asp Glu Gln
                325                 330                 335

Gly Leu Asn Thr His Gly Ala Ser Glu Ile Ser Glu Asp Gln Met Leu
            340                 345                 350

Gly Asp Ser Gln Ser Phe Ser Arg Thr Asp Ser Asp Thr Thr Thr Glu
        355                 360                 365

Thr Ala Pro Gly Lys Gly Lys Leu Arg Ser Gly Ser Asn Thr Gly Leu
    370                 375                 380

Asp Tyr Ile Lys Phe Thr Trp Lys Arg Leu Arg Ser His Ser Arg Gln
385                 390                 395                 400

Tyr Val Ser Gly Leu His Met Asn Arg Glu Arg Lys Ala Ala Lys Gln
                405                 410                 415

Leu Gly Phe Ile Met Ala Ala Phe Ile Leu Cys Trp Ile Pro Tyr Phe
            420                 425                 430

Ile Phe Phe Met Val Ile Ala Phe Cys Lys Asn Cys Cys Asn Glu His
        435                 440                 445

Leu His Met Phe Thr Ile Trp Leu Gly Tyr Ile Asn Ser Thr Leu Asn
    450                 455                 460

Pro Leu Ile Tyr Pro Leu Cys Asn Glu Asn Phe Lys Lys Thr Phe Lys
465                 470                 475                 480

Arg Ile Leu His Ile Arg Ser Met Ala Glu Asp Ala Asp Met Arg Asn
                485                 490                 495

Glu Leu Glu Glu Met Gln Arg Arg Ala Asp Gln Leu Ala Asp Glu Ser
            500                 505                 510

Leu Glu Ser Thr Arg Arg Met Leu Gln Leu Val Glu Glu Ser Lys Asp
        515                 520                 525

Ala Gly Ile Arg Thr Leu Val Met Leu Asp Glu Gln Gly Glu Gln Leu
    530                 535                 540

Glu Arg Ile Glu Glu Gly Met Asp Gln Ile Asn Lys Asp Met Lys Glu
545                 550                 555                 560

Ala Glu Lys Asn Leu Thr Asp Leu Gly Lys Phe Cys Gly Leu Cys Val
                565                 570                 575
```

-continued

```
Cys Pro Cys Asn Lys Leu Lys Ser Ser Asp Ala Tyr Lys Lys Ala Trp
            580                 585                 590
Gly Asn Asn Gln Asp Gly Val Val Ala Ser Gln Pro Ala Arg Val Val
            595                 600             605
Asp Glu Arg Glu Gln Met Ala Ile Ser Gly Gly Phe Ile Arg Arg Val
            610                 615                 620
Thr Asn Asp Ala Arg Glu Asn Glu Met Asp Glu Asn Leu Glu Gln Val
625                 630                 635                 640
Ser Gly Ile Ile Gly Asn Leu Arg His Met Ala Leu Asp Met Gly Asn
                645                 650                 655
Glu Ile Asp Thr Gln Asn Arg Gln Ile Asp Arg Ile Met Glu Lys Ala
            660                 665                 670
Asp Ser Asn Lys Thr Arg Ile Asp Glu Ala Asn Gln Arg Ala Thr Lys
            675                 680                 685
Met Leu Gly Ser Gly Met Glu Asp Ala Lys Asn Ile Lys Lys Gly Pro
690                 695                 700
Ala Pro Phe Tyr Pro Leu Glu Asp Gly Thr Ala Gly Glu Gln Leu His
705                 710                 715                 720
Lys Ala Met Lys Arg Tyr Ala Leu Val Pro Gly Thr Ile Ala Phe Thr
                725                 730                 735
Asp Ala His Ile Glu Val Asn Ile Thr Tyr Ala Glu Tyr Phe Glu Met
            740                 745                 750
Ser Val Arg Leu Ala Glu Ala Met Lys Arg Tyr Gly Leu Asn Thr Asn
            755                 760                 765
His Arg Ile Val Val Cys Ser Glu Asn Ser Leu Gln Phe Phe Met Pro
770                 775                 780
Val Leu Gly Ala Leu Phe Ile Gly Val Ala Val Ala Pro Ala Asn Asp
785                 790                 795                 800
Ile Tyr Asn Glu Arg Glu Leu Leu Asn Ser Met Asn Ile Ser Gln Pro
                805                 810                 815
Thr Val Val Phe Val Ser Lys Lys Gly Leu Gln Lys Ile Leu Asn Val
            820                 825                 830
Gln Lys Lys Leu Pro Ile Ile Gln Lys Ile Ile Ile Met Asp Ser Lys
            835                 840                 845
Thr Asp Tyr Gln Gly Phe Gln Ser Met Tyr Thr Phe Val Thr Ser His
850                 855                 860
Leu Pro Pro Gly Phe Asn Glu Tyr Asp Phe Val Pro Glu Ser Phe Asp
865                 870                 875                 880
Arg Asp Lys Thr Ile Ala Leu Ile Met Asn Ser Ser Gly Ser Thr Gly
                885                 890                 895
Leu Pro Lys Gly Val Ala Leu Pro His Arg Thr Ala Cys Val Arg Phe
            900                 905                 910
Ser His Ala Arg Asp Pro Ile Phe Gly Asn Gln Ile Ile Pro Asp Thr
            915                 920                 925
Ala Ile Leu Ser Val Val Pro Phe His His Gly Phe Gly Met Phe Thr
930                 935                 940
Thr Leu Gly Tyr Leu Ile Cys Gly Phe Arg Val Val Leu Met Tyr Arg
945                 950                 955                 960
Phe Glu Glu Glu Leu Phe Leu Arg Ser Leu Gln Asp Tyr Lys Ile Gln
                965                 970                 975
Ser Ala Leu Leu Val Pro Thr Leu Phe Ser Phe Phe Ala Lys Ser Thr
            980                 985                 990
Leu Ile Asp Lys Tyr Asp Leu Ser  Asn Leu His Glu Ile  Ala Ser Gly
```

| | | | | | | | | | |
|---|---|---|---|---|---|---|---|---|---|
| | | 995 | | | 1000 | | | 1005 | |
| Gly | Ala | Pro | Leu | Ser | Lys | Glu | Val | Gly | Glu | Ala | Val | Ala | Lys | Arg |

Gly Ala Pro Leu Ser Lys Glu Val Gly Glu Ala Val Ala Lys Arg
    1010                1015                1020

Phe His Leu Pro Gly Ile Arg Gln Gly Tyr Gly Leu Thr Glu Thr
    1025                1030                1035

Thr Ser Ala Ile Leu Ile Thr Pro Glu Gly Asp Asp Lys Pro Gly
    1040                1045                1050

Ala Val Gly Lys Val Val Pro Phe Phe Glu Ala Lys Val Val Asp
    1055                1060                1065

Leu Asp Thr Gly Lys Thr Leu Gly Val Asn Gln Arg Gly Glu Leu
    1070                1075                1080

Cys Val Arg Gly Pro Met Ile Met Ser Gly Tyr Val Asn Asn Pro
    1085                1090                1095

Glu Ala Thr Asn Ala Leu Ile Asp Lys Asp Gly Trp Leu His Ser
    1100                1105                1110

Gly Asp Ile Ala Tyr Trp Asp Glu Asp Glu His Phe Phe Ile Val
    1115                1120                1125

Asp Arg Leu Lys Ser Leu Ile Lys Tyr Lys Gly Tyr Gln Val Ala
    1130                1135                1140

Pro Ala Glu Leu Glu Ser Ile Leu Leu Gln His Pro Asn Ile Phe
    1145                1150                1155

Asp Ala Gly Val Ala Gly Leu Pro Asp Asp Asp Ala Gly Glu Leu
    1160                1165                1170

Pro Ala Ala Val Val Val Leu Glu His Gly Lys Thr Met Thr Glu
    1175                1180                1185

Lys Glu Ile Val Asp Tyr Val Ala Ser Gln Val Thr Thr Ala Lys
    1190                1195                1200

Lys Leu Arg Gly Gly Val Val Phe Val Asp Glu Val Pro Lys Gly
    1205                1210                1215

Leu Thr Gly Lys Leu Asp Ala Arg Lys Ile Arg Glu Ile Leu Ile
    1220                1225                1230

Lys Ala Lys Lys Gly Gly Lys Ser Lys Leu
    1235                1240

<210> SEQ ID NO 5
<211> LENGTH: 4767
<212> TYPE: DNA
<213> ORGANISM: Artificial
<220> FEATURE:
<223> OTHER INFORMATION: cloning construct

<400> SEQUENCE: 5
gcgtttaaac ttaagctatg ctttccatg tggaaggact gatagctatc atcgtgttct      60
accttctaat tttgctggtt ggaatatggg ctgcctggag aaccaaaaac agtggcagcg     120
cagaagagcg cagcgaagcc atcatagttg gtggccgaga tattggttta ttggttggtg     180
gatttaccat gacagctacc tgggtcggag gagggtatat caatggcaca gctgaagcag     240
tttatgtacc aggttatggc ctagcttggg ctcaggcacc aattggatat tctcttagtc     300
tgattttagg tggcctgttc tttgcaaaac ctatgcgttc aaaggggtat gtgaccatgt     360
tagacccgtt tcagcaaatc tatggaaaac gcatgggcgg actcctgttt attcctgcac     420
tgatgggaga aatgttctgg gctgcagcaa ttttctctgc tttgggagcc accatcagcg     480
tgatcatcga tgtggatatg cacatttctg tcatcatctc tgcactcatt gccactctgt     540
acacactggt gggagggctc tattctgtgg cctacactga tgtcgttcag ctctttttgca     600

```
tttttgtagg gctgtggatc agcgtcccct ttgcattgtc acatcctgca gtcgcagaca    660
tcgggttcac tgctgtgcat gccaaatacc aaaagccgtg gctgggaact gttgactcat    720
ctgaagtcta ctcttggctt gatagttttc tgttgttgat gctgggtgga atcccatggc    780
aagcatactt tcagagggtt ctctcttctt cctcagccac ctatgctcaa gtgctgtcct    840
tcctggcagc tttcgggtgc ctggtgatgg ccatcccagc catactcatt ggggccattg    900
gagcatcaac agactggaac cagactgcat atgggcttcc agatcccaag actacagaag    960
aggcagacat gattttacca attgttctgc agtatctctg ccctgtgtat atttctttct   1020
ttggtcttgg tgcagtttct gctgctgtta tgtcatcagc agattcttcc atcttgtcag   1080
caagttccat gtttgcacgg aacatctacc agctttcctt cagacaaaat gcttcggaca   1140
aagaaatcgt ttgggttatg cgaatcacag tgtttgtgtt tggagcatct gcaacagcca   1200
tggccttgct gacgaaaact gtgtatgggc tctggtacct cagttctgac cttgtttaca   1260
tcgttatctt cccccagctg ctttgtgtac tctttgttaa gggaaccaac acctatgggg   1320
ccgtggcagg ttatgtttct ggcctcttcc tgagaataac tggaggggag ccatatctgt   1380
atcttcagcc cttgatcttc taccctggct attaccctga tgataatggt atatataatc   1440
agaaatttcc atttaaaaca cttgccatgg ttacatcatt cttaaccaac atttgcatct   1500
cctatctagc caagtatcta tttgaaagtg gaaccttgcc acctaaatta gatgtatttg   1560
atgctgttgt tgcaagacac agtgaagaaa acatggataa gacaattctt gtcaaaaatg   1620
aaaatattaa attagatgaa cttgcacttg tgaagccacg acagagcatg accctcagct   1680
caactttcac caataaagag gccttccttg atgttgattc cagtccagaa gggtctggga   1740
ctgaagataa tttacagatg agtaaaggag aagaactttt cactggagtt gtcccaattc   1800
ttgttgaatt agatggtgat gttaatgggc acaaattttc tgtcagtgga gagggtgaag   1860
gtgatgcaac atacggaaaa cttacccttta aatttatttg cactactgga aaactacctg   1920
ttccatggcc aacacttgtc actactttct cttatggtgt tcaatgcttt tcaagatacc   1980
cagatcatat gaaacagcat gactttttca agagtgccat gcccgaaggt tatgtacagg   2040
aaagaactat atttttcaaa gatgacggga actacaagac acgtgctgaa gtcaagtttg   2100
aaggtgatac ccttgttaat agaatcgagt taaaggtat tgattttaaa gaagatggaa   2160
acattcttgg acacaaattg gaatacaact ataactcaca atgtatac atcatggcag   2220
acaaacaaaa gaatggaatc aaagttaact tcaaaattag acacaacatt gaagatggaa   2280
gcgttcaact agcagaccat tatcaacaaa atactccaat tggcgatggc cctgtccttt   2340
taccagacaa ccattacctg tccacacaat ctgcccttc gaaagatccc aacgaaaaga   2400
gagaccacat ggtccttctt gagtttgtaa cagctgctgg gattacacat ggcatggatg   2460
aactatacaa aatggccgaa gacgcagaca tgcgcaatga gctggaggag atgcagcgaa   2520
gggctgacca gttggctgat gagtcgctgg aaagcacccg tcgtatgctg caactggttg   2580
aagagagtaa agatgctggt atcaggactt tggttatgtt ggatgaacaa ggagaacaac   2640
tggaacgcat tgaggaaggg atggaccaaa tcaataagga catgaaagaa gcagaaaaga   2700
atttgacgga cctaggaaaa ttctgcgggc tttgtgtgtg tccctgtaac aagcttaaat   2760
caagtgatgc ttacaaaaaa gcctggggca ataatcagga cggagtggtg gccagccagc   2820
ctgctcgtgt agtggacgaa cgggagcaga tggccatcag tggcggcttc atccgcaggg   2880
taacaaatga tgcccgagaa aatgaaatgg atgaaaacct agagcaggtg agcggcatca   2940
```

```
                                        -continued tcgggaacct ccgtcacatg gccctggata tgggcaatga gatcgataca cagaatcgcc      3000
agatcgacag gatcatggag aaggctgatt ccaacaaaac cagaattgat gaggccaacc      3060
aacgtgcaac aaagatgctg ggaagtggta tggaagacgc caaaaacata agaaaggcc       3120 cggcgccatt ctatcctcta gaggatgaa  ccgctggaga gcaactgcat aaggctatga      3180
agagatacgc cctggttcct ggaacaattg cttttacaga tgcacatatc gaggtgaaca      3240
tcacgtacgc ggaatacttc gaaatgtccg ttcggttggc agaagctatg aaacgatatg      3300
ggctgaatac aaatcacaga atcgtcgtat gcagtgaaaa ctctcttcaa ttctttatgc      3360
cggtgttggg cgcgttattt atcggagttg cagttgcgcc cgcgaacgac atttataatg      3420
aacgtgaatt gctcaacagt atgaacattt cgcagcctac cgtagtgttt gtttccaaaa      3480
aggggttgca aaaattttg  aacgtgcaaa aaaaattacc aataatccag aaaattatta      3540
tcatggattc taaaacggat taccagggat ttcagtcgat gtacacgttc gtcacatctc      3600
atctacctcc cggttttaat gaatacgatt ttgtaccaga gtcctttgat cgtgacaaaa      3660
caattgcact gataatgaat tcctctggat ctactgggtt acctaagggt gtggcccttc      3720
cgcatagaac tgcctgcgtc agattctcgc atgccagaga tcctattttt ggcaatcaaa      3780
tcattccgga tactgcgatt ttaagtgttg ttccattcca tcacggtttt ggaatgttta      3840
ctacactcgg atatttgata tgtggatttc gagtcgtctt aatgtataga tttgaagaag      3900
agctgttttt acgatcccctt caggattaca aaattcaaag tgcgttgcta gtaccaaccc      3960
tattttcatt cttcgccaaa agcactctga ttgacaaata cgatttatct aatttacacg      4020
aaattgcttc tgggggcgca cctctttcga agaagtcgg ggaagcggtt gcaaaacgct       4080
tccatcttcc agggatacga caaggatatg ggctcactga gactacatca gctattctga      4140
ttacacccga gggggatgat aaaccgggcg cggtcggtaa agttgttcca ttttttgaag      4200
cgaaggttgt ggatctggat accgggaaaa cgctgggcgt taatcagaga ggcgaattat      4260
gtgtcagagg acctatgatt atgtccggtt atgtaaacaa tccggaagcg accaacgcct      4320
tgattgacaa ggatggatgg ctacattctg gagacatagc ttactgggac gaagacgaac      4380
acttcttcat agttgaccgc ttgaagtctt taattaaata caaaggatat caggtggccc      4440
ccgctgaatt ggaatcgata ttgttacaac accccaacat cttcgacgcg ggcgtggcag      4500
gtcttcccga cgatgacgcc ggtgaacttc ccgccgccgt tgttgttttg gagcacggaa      4560
agacgatgac ggaaaaagag atcgtggatt acgtcgccag tcaagtaaca accgcgaaaa      4620
agttgcgcgg aggagttgtg tttgtggacg aagtaccgaa aggtcttacc ggaaaactcg      4680
acgcaagaaa aatcagagag atcctcataa aggccaagaa gggcggaaag tccaaattgt      4740
agctcgagtc tagagggccc gtttaaa                                         4767
```

METHODS FOR THE DETERMINATION OF THE BIOLOGICAL ACTIVITIES OF NEUROTOXIN POLYPEPTIDES

The present invention pertains to a method for determining the biological activity of a neurotoxin, the method comprising the steps of: (a) expressing a fusion protein comprising (i) an anchor protein, (ii) a reporter protein and (iii) a neurotoxin cleavage site intervening the anchor protein and the reporter protein, in neurotoxin-sensitive cells; (b) incubating the neurotoxin-sensitive cells of (a) with a neurotoxin and cultivating the cells under conditions which allow the neurotoxin to exert its biological activity; (c) permeabilizing the neurotoxin-sensitive cells of (b) under conditions which allow the release of the reporter protein but not the release of the anchor protein from the permeabilized neurotoxin-sensitive cells; and (d) quantifying the activity of the reporter protein released from the cells, thereby determining the biological activity of the neurotoxin. In addition, the invention relates to a fusion protein comprising (i) an anchor protein, (ii) a reporter protein, and (iii) a neurotoxin cleavage site intervening the anchor protein and the reporter protein, for determining the biological activity of a neurotoxin, in neurotoxin-sensitive cells. Further encompassed by the present invention is a kit comprising the fusion protein of the invention. Finally, the invention pertains to the use of a fusion protein of the invention for determining the biological activity of a neurotoxin, in neurotoxin-sensitive cells.

*Clostridium botulinum* and *Clostridium tetani* produce highly potent neurotoxins, i.e. botulinum toxins (BoNTs) and tetanus toxin (TeNT), respectively. These Clostridial neurotoxins (CNTs) specifically bind to neuronal cells and disrupt neurotransmitter release. Each toxin is synthesized as an inactive unprocessed, approximately 150 kDa single-chain protein. The posttranslational processing involves formation of disulfide bridges, and limited proteolysis (nicking) by the bacterial protease(s). Active neurotoxin consists of two chains, an N-terminal light chain of approx. 50 kDa and a heavy chain of approx. 100 kDa linked by a disulfide bond. CNTs structurally and functionally consist of three domains, i.e. the catalytic light chain, the heavy chain encompassing the translocation domain (N-terminal half) and the receptor binding domain (C-terminal half); see, e.g., Krieglstein 1990, Eur. J. Biochem. 188, 39; Krieglstein 1991, Eur. J. Biochem. 202, 41; Krieglstein 1994, J. Protein Chem. 13, 49. The Botulinum neurotoxins are synthesized as molecular complexes comprising the 150 kDa neurotoxin protein and associated non-toxic proteins. The complex sizes differ based on the Clostridial strain and the distinct neurotoxin serotypes ranging from 300 kDa, over 500 kDa, and 900 kDa. The non-toxic proteins in these complexes stabilize the neurotoxin and protect it against degradation; see Silberstein 2004, Pain Practice 4, S19-S26.

*Clostridium botulinum* secretes seven antigenically distinct serotypes designated A to G of the botulinum neurotoxin (BoNT). All serotypes together with the related tetanus neurotoxin (TeNT) secreted by *Clostridium tetani*, are $Zn^{2+}$-endoproteases that block synaptic exocytosis by cleaving SNARE proteins; see Couesnon, 2006, Microbiology, 152, 759. CNTs cause the flaccid muscular paralysis seen in botulism and tetanus; see Fischer 2007, PNAS 104, 10447.

Despite its toxic effects, botulinum toxin complex has been used as a therapeutic agent in a large number of diseases. Botulinum toxin serotype A was approved for human use in the United States in 1989 for the treatment of strabism, blepharospasm, and other disorders. It is commercially available as Botulinum toxin A (BoNT/A) protein preparation, for example, under the trade name BOTOX (Allergan, Inc.) or under the trade name DYSPORT/RELOXIN (Ipsen, Ltd). An improved, complex-free Botulinum toxin A preparation is commercially available under the trade name XEOMIN (Merz Pharmaceuticals, GmbH). For therapeutic applications, the preparation is injected directly into the muscle to be treated. At physiological pH, the toxin is released from the protein complex and the desired pharmacological effect takes place. The effect of Botulinum toxin is only temporary, which is the reason why repeated administration of Botulinum toxin may be required to maintain a therapeutic affect.

The Clostridial neurotoxins weaken voluntary muscle strength and are effective therapy for strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction; see Jost 2007, Drugs 67, 669.

During the manufacturing process of Clostridial neurotoxins, the qualitative and quantitative determination of said neurotoxins as well as the quality control of the biologically active neurotoxin polypeptides is of particular importance. In addition, governmental agencies accept only simple, reliable, and validated Botulinum toxin activity assays. At present the mouse $LD_{50}$ bioassay, a lethality test, remains the "gold standard" used by pharmaceutical manufacturers to analyze the potency of their preparations; see Arnon et al. (2001), JAMA 285, 1059-1070. However, in recent years, considerable effort has been undertaken to seek for alternative approaches to alleviate the need for animal testing and all the disadvantages, costs and ethical concerns associated with animal-based assays. In addition, the regulatory agencies are engaging pharmaceutical companies to apply the three "Rs" principle to the potency testing of Botulinum neurotoxins: "Reduce, Refine, Replace"; see Straughan, Altern. Lab. Anim. (2006), 34, 305-313. As a consequence, cell-based test systems have been developed in order to provide reasonable alternatives to methods using live animals. Yet, only three cellular test systems are available for the determination of neurotoxin biological activity thus far which have been shown to be sufficiently sensitive to neurotoxin polypeptides. These cell-based test systems include the use of primary neurons isolated from rodent embryos which are differentiated in vitro (Pellett et al. (2011), Biochem. Biophys. Res. Commun. 404, 388-392), neuronal differentiated induced pluripotent stem cells (Whitemarsh et al. (2012), Toxicol. Sci. 126, 426-35), and a subclone of the SiMa cell line (WO 2010/105234 A1).

However, the isolation of primary neurons requires the killing of animals and is laborious and time consuming. Furthermore, test systems using different primary neurons show large variances. Similarly, the generation of neuronal differentiated induced pluripotent stem cells is difficult and time consuming. In addition, storage of such cells is very problematic. Assays using tumor cell lines are frequently not sensitive enough to BoNTs. Moreover, complex differentiation protocols are required for said tumor cell lines which result in large variances and/or high failure rates of assays using said cell lines.

In light of the above, further test systems for the determination of neurotoxin polypeptide activity acceptable to governmental agencies are highly desirable. In addition, alternatives to animal-based test systems are needed.

Thus, the technical problem underlying the present invention may be seen as the provision of means and methods complying with the aforementioned needs. The technical problem is solved by the embodiments characterized in the claims and herein below.

The present invention relates, in a first aspect, to a method for determining the biological activity of a neurotoxin, the method comprising the steps of:

(a) expressing a fusion protein comprising (i) an anchor protein, (ii) a reporter protein and (iii) a neurotoxin cleavage site intervening the anchor protein and the reporter protein, in neurotoxin-sensitive cells;

(b) incubating the neurotoxin-sensitive cells of (a) with a neurotoxin and cultivating the neurotoxin-sensitive cells under conditions which allow the neurotoxin to exert its biological activity;

(c) permeabilizing the neurotoxin-sensitive cells of (b) under conditions which allow the release of the reporter protein but not the release of the anchor protein from the permeabilized neurotoxin-sensitive cells; and (d) quantifying the activity of the reporter protein released from the permeabilized neurotoxin-sensitive cells of (c), thereby determining the biological activity of the neurotoxin.

In cell-based test systems for determining the biological activity of neurotoxin polypeptides described in the art, cells are differentiated into neuronal cells in order to obtain a sufficient sensitivity for the neurotoxin polypeptide. Subsequently, these cells are incubated with the neurotoxin polypeptide. Thereafter, the amount of cleaved neurotoxin substrate is determined, normally by using specific antibodies. For an accurate determination of the biological activity of a neurotoxin polypeptide, three neurotoxin substrate-specific antibodies of high quality are required from three different host species. This includes a capture antibody in order to separate the substrate of the neurotoxin polypeptide, such as the BoNT/A substrate SNAP-25, from the other cellular proteins. The capture antibody is frequently directed against an N-terminal region of the neurotoxin substrate, e.g., the N-terminal region of SNAP-25. Further, a neo-epitope specific antibody is necessary for the detection of the neurotoxin-cleaved substrate, for example, the BoNT/A-cleaved SNAP-25. An additional detection antibody is required which is generally directed against the C-terminal region of the neurotoxin substrate, for instance, the C-terminal region of SNAP-25, in order to determine the total amount of neurotoxin substrate, or the amount of non-cleaved neurotoxin substrate, to allow for a standardization.

The method for determining the biological activity of a neurotoxin polypeptide of the present invention is based on a neurotoxin-sensitive cell genetically modified to express a novel fusion protein of the invention. The neurotoxin-sensitive cells can be cells from or derived from tumor cell lines, primary cells, stem cells, induced pluripotent stem cells or other cells defined elsewhere herein. "Derived from" means that the neurotoxin-sensitive cells stem from the indicated cells including, e.g., clones or subclones thereof. Such clones or subclones can be non-modified or genetically modified, in comparison to the parental cells. In certain aspects, the neurotoxin-sensitive cells are able to differentiate into neuronal cells. In these cases, the neurotoxin-sensitive cells are differentiated in a culture medium under conditions and for a time period which allows for the differentiation of the neurotoxin-sensitive cells into neuronal differentiated cells. The fusion protein of the present invention comprises an anchor protein, a neurotoxin polypeptide cleavage site and a reporter protein as defined more specifically elsewhere herein. For example, the fusion protein encompasses a transmembrane protein or membrane-associated protein as an anchor protein, a reporter protein and a neurotoxin cleavage site. The cleavage site for the neurotoxin polypeptide is positioned between the anchor protein and the reporter protein. In a first step of the method of the invention, a polynucleotide sequence encoding the mentioned fusion protein is introduced into neurotoxin-sensitive cells which are then cultivated under conditions which allow for the expression of the (biologically active) fusion protein. In certain aspects of the methods of the invention, the expression of the fusion protein of the invention is induced by inducible expression systems known in the art, e.g., a tetracycline-inducible expression system (Zhou, X., Vink, M., Klave, B., Berkhout, B. & Das, A. T. (2006) Optimization of the Tet-On system for regulated gene expression through viral evolution. Gene Ther. 13(19): 1382-1390), mifepristone-inducible expression system (Wang, Y., B. W. O'Malley, J., Tsai, S. Y., and O'Malley, B. W. (1994). A Regulatory System for Use in Gene Transfer. Proc. Natl. Acad. Sci. USA 91, 8180-8184), ecdysone-inducible expression system (No D, Yao T P, Evans R M. Ecdysone-inducible gene expression in mammalian cells and transgenic mice. Proc Natl Acad Sci USA. 1996 Apr. 16; 93(8): 3346-51; Meyer-Ficca M L, Meyer R G, Kaiser H, Brack A R, Kandolf R, Küpper J H. Comparative analysis of inducible expression systems in transient transfection studies. Anal Biochem. 2004 Nov. 1; 334(1): 9-19) or the like which are commercially available (Clontech; Life Technologies; Agilent). Subsequently, the neurotoxin-sensitive cells are incubated with a neurotoxin polypeptide cultivated for a time period (such as about 24 to 72 hours) and under conditions which allow the neurotoxin to exert its biological activity. Upon cleavage by the proteolytic activity of the neurotoxin polypeptide at the neurotoxin polypeptide cleavage site of the fusion protein, the reporter protein is released into the cell. The intoxication step can optionally be followed by a wash step. The neurotoxin-sensitive cells are thereafter permeabilized, for instance, by a hemolysin, for a time period and under conditions which allow the release of the reporter protein but not the release of the anchor protein from the permeabilized neurotoxin-sensitive cells. Subsequently, the supernatant comprising the reporter protein is recovered and, where appropriate, further processed, e.g., filtrated or centrifuged, before the activity of the reporter protein is determined. By quantifying the activity of the reporter protein released from the cells, the biological activity of the neurotoxin polypeptide can be determined.

The methods of testing the biological activity of neurotoxin polypeptides of the present invention showed improved sensitivity, in comparison to methods known in the art. In addition, the methods of the invention showed higher precision and robustness, due to the simple handling. These technical and qualitative benefits of the methods of the invention are demonstrated in the following Example.

Clostridial neurotoxins are characterized in that they specifically inhibit the secretion of neurotransmitters from pre-synaptic nerve endings. The selectivity for peripheral neurons is mediated by the recognition of two different receptors, SV2 and GT1b. The physiological effect of the neurotoxins is based on the cleavage of a protein of the so-called SNARE complex subsequent to the binding of the receptor and the translocation of the neurotoxin's light chain. The determination of the biological activity of BoNTs is an important aspect in the characterization of said neurotoxin proteins and is required, inter alia, by regulatory authorities for the clearance of BoNT-containing products. A reliable test for the measurement of the biological activity of BoNTs is, therefore, basis for research, development and marketing of products containing BoNTs. Furthermore, cell-based test systems shall replace the thus far predominant animal tests, for ethical reasons. For establishing such cell-based test systems, a sufficient high sensitivity of neuronal cells or cell lines towards Botulinum neurotoxins is essential. However, in order to obtain such high sensitivity, laborious differentiation methods of neuronal cell lines are required so far. As a result, only a few cell-based test systems are available yet, as indicated above. To determine the biological activity of Botulinum toxins in pharmaceutical products, the neuronal cells or cell lines shall have the following properties: First, the cells shall be of human, neuronal origin in order to resemble the target as close as possible, i.e. the human patient. Second, the cell system shall be robust towards excipients in the final product and, preferably, also towards impurities in intermediate stages of the production process (process controls). Third, the cell-based test system shall exhibit a dynamic measuring range which allows for the accurate determination of the biological activity of BoNTs in a vial (for example, 50 U, 100 U or 200 U BoNT/A). Considering technical factors such as the solubility of excipients, volumes of cell culture media etc., a BoNT concentration of less than 1 pM has to be determined accurately. According to the inventors' best knowledge, only three cell-based test systems are available so far which show sufficiently high sensitivity to BoNTs. These include primary neurons of embryos from rodents, neuronal differentiated induced pluripotent stem cells and a subclone of the SiMa cell line, as already mentioned elsewhere herein. However, said cells or cell lines have been reported to exhibit a sufficiently high sensitivity, only after complex and laborious differentiation protocols, which are frequently associated with large variances. In contrast, the present invention provides for a simple, reliable and robust cell-based test system for the measurement of the biological activity of Botulinum neurotoxins (BoNT) which fulfills the abovementioned requirements and which has been further improved with respect to sensitivity, in comparison to the cellular test systems described in the art.

The term "polypeptide" or "protein" as used herein encompasses isolated or purified polypeptides being essentially free of other host cell polypeptides. The mentioned term includes a fusion protein. Fusion proteins or chimeric proteins (literally, made of parts from different sources) are proteins created through the joining of two or more genes that originally coded for separate proteins. Translation of this fusion gene results in a single protein with functional properties derived from each of the original proteins. Recombinant fusion proteins are created artificially by recombinant DNA technology known in the art; see, e.g., Sambrook, Molecular Cloning: A Laboratory Manual, Cold Spring Harbor Laboratory, third edition, 2001. Chimeric proteins or chimera usually designate hybrid proteins made of polypeptides having different functions or physicochemical patterns. Moreover, the term "fusion protein" includes, in an aspect, chemically modified fusion proteins. Such modifications may be artificial modifications such as mutations, e.g., point mutations, substitutions, deletions, insertions and the like, or naturally occurring modifications such as post-translational modifications, e.g., glycosylation, phosphorylation, palmitoylation, myristoylation and the like. The fusion protein shall have the biological properties referred to herein. More specifically, the term "fusion protein" or "fusion polypeptide" as used herein, comprises an anchor protein, a reporter protein and a neurotoxin cleavage site. The "anchor protein" as used herein is a polypeptide which is stably attached to or integrated into the plasma membrane and in contact with the cytosol of the neurotoxin-sensitive cell. Accordingly, the anchor protein can be a (trans)membrane or integral membrane protein or a membrane-associated protein. The anchor protein of the fusion protein is located in (for a (trans)membrane or integral membrane protein) or at (in case of a membrane-associated protein) the plasma membrane, both in the un-cleaved and neurotoxin-cleaved status. It is immediately evident to those skilled in the art that proteins which are temporarily attached to or only partially associated with the plasma membrane are not suitable as anchor protein. The plasma membrane includes the cell membrane and vesicle membrane. The transmembrane protein is, for example, a choline transporter (NP_068587), histamine H1 receptor (H1-receptor, NP_001091683), or any other G protein-coupled receptor (GPCR; e.g. AAI28124, NP_000675, P08172) or SV2 (NP_055664). The membrane-associated protein can be, e.g., SNAP-25 (P60880), MARCKS Protein (NP_002347), or C2 domain containing proteins (e.g. NP_002728; NP_002730) Encompassed are also fragments of such anchor proteins having the mentioned biological properties. The "neurotoxin cleavage site" as used herein is a BoNT/A, BoNT/B, BoNT/C1, BoNT/D, BoNT/D, BoNT/E, BoNT/F, BoNT/G or TeNT cleavage site, preferably a BoNT/A, BoNT/C1 or BoNT/E cleavage site. Neurotoxin cleavage sites are recognized and cleaved by neurotoxin polypeptides. The corresponding sequences of neurotoxin cleavage sites are known in the art and described, for example, in Binz et al. (2010), Toxins, 2(4), pp. 665-682, WO 2010/124998 or WO 2010/105234 A1, the disclosure content of which is incorporated herewith by reference. The neurotoxin cleavage site is positioned between the anchor protein and the reporter protein and accessible to the neurotoxin polypeptide from the cytosol of the neurotoxin-sensitive cell. Upon cleavage by the proteolytic activity of the neurotoxin polypeptide at the neurotoxin polypeptide cleavage site of the fusion protein, the reporter protein is released into the cytosol of the neurotoxin-sensitive cell, whereas the anchor protein remains in or at the plasma membrane. The "reporter protein" or "detection protein" (both terms are interchangeable) as used herein is a detectable marker, for instance, an enzyme like luciferase, alkaline phosphatase, beta-galactosidase, or horseradish peroxidase. Alternatively, the reporter protein can be a fluorescent protein, for example, GFP, BFP, YFP, RFP or the like. The reporter protein of the fusion protein is localized at the plasma membrane in the non-cleaved status and released into the cytosol upon cleavage by the neurotoxin polypeptide. Encompassed are also fragments of such reporter proteins having the mentioned biological properties. The arrangement of the fusion protein can be anchor protein-neurotoxin cleavage site-reporter protein or reporter protein-neurotoxin cleavage site-anchor protein. The fusion protein can further comprise one or more linker regions, such as poly-Glycine linkers or the like. The linker can be used, e.g., to link the anchor protein and the neurotoxin cleavage site, or the neurotoxin cleavage site and the reporter protein, in the fusion protein. It is also envisaged that two or more linkers are used in the fusion protein, e.g., one linker between the anchor protein and the neurotoxin cleavage site and a further linker between the neurotoxin cleavage site and the reporter protein. The linker can be the same or be different. Encompassed is also a linker between the anchor protein and the reporter protein that can comprise one or more (e.g. two, three or even more) neurotoxin cleavage site(s). The term "linker" or "linker region" as used herein denotes a polylinker which is a short segment of amino acid sequence. Suitable linker sequences encoded by a corresponding DNA sequence are described, for example, in Schiavo G, Matteoli M, Montecucco C: Neurotoxins affecting neuroexocytosis. Physiol. Rev. 2000, 80: 717-66. Besides the basic role in linking the functional proteins together (as in flexible or rigid linkers), linkers may offer many other advantages for the production of fusion proteins, such as improving biological activity, increasing expression yield, and achieving desirable pharmacokinetic profiles; see, e.g., Chen et al., Adv. Drug Deliv. Rev. 2013, 65(10), pp. 1357-69. In addition, the fusion protein can encompass suitable tags, e.g., FLAG-tags, Myc-tags, His-tags, HA-tags or GST-tags which allow, e.g., for efficient isolation and/or purification of the tagged fusion protein or constituents thereof such as the reporter protein. The tag(s) can be attached to the fusion protein via a linker, if appropriate. It is also envisaged by the scope of the invention that the fusion protein comprises a standardization or normalization factor. The standardization or normalization factor can also be attached to the fusion protein via a linker, if appropriate. For example, GFP is used as a standardization factor or normalization factor, in the choline transporter-GFP-SNAP-25-luciferase fusion protein of the invention. The introduction of such a further component for the normalization or correction of each measurement or measured value can be used for reduction of the statistical variance of individual measurements. In the course of assays, different expression rates, cell numbers, material losses or the like will occur randomly or systematically, so that the measured values are subject to a statistical error. By introduction of a correction factor, the individual measurements can be compared with each other more easily. For example, if during cultivation of cells different expression rates occur, or if there are different losses of cell material during wash steps, this will be predictable by the measurement of the correction factor. The fusion protein, in an aspect, can be manufactured by chemical synthesis or recombinant molecular biology techniques well known for the skilled artisan; see, e.g., Sambrook, Molecular Cloning: A Laboratory Manual, Cold Spring Harbor Laboratory, third edition, 2001. In an aspect, such a method of manufacturing the fusion protein comprises (a) culturing the host cell described elsewhere herein in more detail and (b) obtaining from the said host cell the fusion protein. In an aspect of this method, the fusion protein can be obtained by conventional purification techniques, e.g., from a host cell lysate including affinity chromatography, ion exchange chromatography, size exclusion chromatography and/or preparative gel electrophoresis. The term "polypeptide" or "protein" in another aspect includes polypeptide preparations comprising the fusion protein and other proteins in addition.

The term "neurotoxin-sensitive cell" as used herein means a cell which is susceptible to a neurotoxin polypeptide exhibiting the biological properties characteristic for a neurotoxin polypeptide, namely, (a) receptor binding, (b) internalization, (c) translocation across the endosomal membrane into the cytosol, and/or (d) endoproteolytic cleavage of proteins involved in synaptic vesicle membrane fusion, mentioned elsewhere herein. Accordingly, a "neurotoxin-sensitive cell" as referred to herein is susceptible to neurotoxin intoxication. A cell susceptible to neurotoxin intoxication is preferably susceptible to a biologically active or mature neurotoxin polypeptide as defined herein. By definition, a "cell susceptible to neurotoxin intoxication" must express, or be engineered to express, at least one neurotoxin receptor and at least one neurotoxin substrate. Receptors and substrates for neurotoxins are described in the art. The term "neurotoxin-sensitive cell" as used herein comprises a cell or a cell line, for example, an isolated, primary cell or a cell line thereof or a cell of an established cell line or an established cell line, such as a neuroblastoma cell or neuroblastoma cell line as defined herein. The neurotoxin-sensitive cells as denoted herein include cells, e.g., tumor cells which are able to differentiate into neuronal cells, under appropriate cell culture conditions. Such cells encompass, for instance, cells from tumor cell lines, e.g., Neuro-2a cells, PC12 cells, NG108-15 cells, P19 cells, SiMa cells or SH-SY5Y cells, primary cells, stem cells, induced pluripotent stem cells, cells derived therefrom or other cells defined elsewhere herein and used in the following examples. The term "susceptible to neurotoxin intoxication" as denoted herein means a cell that can undergo the overall cellular mechanisms whereby a neurotoxin polypeptide (e.g., BoNT/A) cleaves a neurotoxin substrate (e.g., the BoNT/A substrate SNAP-25) and encompasses the binding of the neurotoxin to its corresponding receptor (e.g., binding of BoNT/A to BoNT/A receptor), the internalization of the neurotoxin/receptor complex, the translocation of the neurotoxin light chain from an intracellular vesicle into the cytoplasm, and/or the proteolytic cleavage of the neurotoxin substrate, preferably all of the mentioned mechanisms. As appreciated by those skilled in the art, the neurotoxin-sensitive cell is preferably able to first uptake a neurotoxin and then undergoes the overall cellular mechanisms listed above. A neurotoxin-sensitive cell as used herein can uptake, e.g., about 100 nanomolar (nM), about 10 nM, about 1 nM, about 500 picomolar (pM), about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 9 pM, about 8 pM, about 7 pM, about 6 pM, about 5 pM, about 4 pM, about 3 pM, about 2 pM, about 1 pM, about 0.5 pM, or about 0.1 pM of neurotoxin polypeptide or even less than one of the indicated values. EC50 values above 100 pM have been reported in the literature. Preferably, the "neurotoxin-sensitive cell" as used herein is susceptible to neurotoxin intoxication by, e.g., about 1 nM or less, 500 pM or less, about 400 pM or less, about 300 pM or less, about 200 pM or less, about 100 pM or less, about 90 pM or less, about 80 pM or less, about 70 pM or less, about 60 pM or less, about 50 pM or less, about 40 pM or less, about 30 pM or less, about 20 pM or less, about 10 pM or less, about 9 pM or less, about 8 pM or less, about 7 pM or less, about 6 pM or less, about 5 pM or less, about 4 pM or less, about 3 pM or less, about 2 pM or less, about 1 pM or less, about 0.9 pM or less, about 0.8 pM or less, about 0.7 pM or less, about 0.6 pM or less, about 0.5 pM or less, about 0.4 pM or less, about 0.3 pM or less, about 0.2 pM or less, or even about 0.1 pM or less. Assays for determining the biological activity of a neurotoxin polypeptide are well known in the art and also described elsewhere herein (see, e.g., Pellett et al., Withemarsh et al. Toxicological Sciences 126(2), 426-435 (2012), WO 2010/105234 A1)

As known in the art, the "half maximal effective concentration (EC50)" refers to the concentration of a drug, antibody or toxicant which induces a response halfway between the baseline and maximum after some specified exposure time. It is commonly used as a measure of drug's potency. The EC50 of a graded dose response curve therefore represents the concentration of a compound where 50% of its maximal effect is observed. The EC50 of a quantal dose response curve represents the concentration of a compound where 50% of the population exhibits a response, after a specific exposure duration.

Methods for the identification and/or isolation of cells or cell lines susceptible to neurotoxin intoxication and/or having neurotoxin uptake capacity, i.e. neurotoxin-sensitive cells as defined herein, are known in the art; see, e.g. US 2012/0122128 A1. The biological activity of the neurotoxin polypeptides, in an aspect, results from all of the aforementioned biological properties. Cell-based systems for determining the biological activity of neurotoxins known in the art have been indicated elsewhere herein. In vivo assays for assessing the biological activity of neurotoxins include, for example, the already mentioned mouse $LD_{50}$ assay and the ex vivo mouse hemidiaphragm assay as described by Pearce et al. and Dressier et al.; see Pearce 1994, Toxicol. Appl. Pharmacol. 128: 69-77 and Dressier 2005, Mov. Disord. 20:1617-1619. As known to those skilled in the art, the biological activity of neurotoxins is commonly expressed in Mouse Units (MU). One MU is the amount of neurotoxic component, which kills 50% of a specified mouse population after intraperitoneal injection, i.e. the mouse i.p. LD 50. The method of the invention provides for a simple, reliable, and robust cell-based test system with increased sensitivity to neurotoxin polypeptides, in comparison to the cellular test systems described in the art which require complex differentiation protocols. Accordingly, the method of the invention provides for an improved alternative to the cellular test systems of the art for determining the biological activity of neurotoxins. Further, the method of the invention can be used as an alternative to animal-based assays.

The terms "differentiation", "differentiating" or "differentiated" as used herein denote the process by which an unspecialized or a relatively less specialized cell becomes relatively more specialized. In the context of cell ontogeny, the adjective "differentiated" is a relative term. Hence, a "differentiated cell" is a cell that has progressed further down a certain developmental pathway than the cell it is being compared with. A differentiated cell may, for example, be a terminally differentiated cell, i.e., a fully specialized cell that takes up specialized functions in various tissues and organs of an organism, and which may but need not be post-mitotic. In another example, a differentiated cell may also be a progenitor cell within a differentiation lineage, which can further proliferate and/or differentiate. Similarly, a cell is "relatively more specialized" if it has progressed further down a certain developmental pathway than the cell it is being compared with, wherein the latter is therefore considered "unspecialized" or "relatively less specialized". A relatively more specialized cell may differ from the unspecialized or relatively less specialized cell in one or more demonstrable phenotypic characteristics, such as, for example, the presence, absence or level of expression of particular cellular components or products, e.g., RNA, proteins, specific cellular markers or other substances, activity of certain biochemical pathways, morphological appearance, proliferation capacity and/or kinetics, differentiation potential and/or response to differentiation signals, etc., wherein such characteristics signify the progression of the relatively more specialized cell further along the said developmental pathway.

The term "neuronal differentiated cell" as used herein means a cell which has reached the final neuronal differentiation status. For example, the murine embryonic carcinoma P19 cells differentiate first to neuro-progenitor cells before they further differentiate to neurons. The neuro-differentiation process can be followed, e.g., phenotypically (by phase-contrast microscopy) and/or by the expression of neuronal differentiation markers; see, e.g., Babuska et al. (2010), Prague Medical Report 111, 289-299 or Migliore and Shepherd, Nature Reviews Neuroscience 6, 810-818 (2005). Assays which can be used for the determination of the expression of said neuronal differentiation markers include, for example, PCR, RT-PCR, Northern blot, Western blot or Dot blot, immunoprecipitation analysis, enzyme-linked immunosorbent analysis (ELISA) or FACS analysis which are known in the art; see, e.g., Sambrook, Molecular Cloning: A Laboratory Manual, Cold Spring Harbor Laboratory, third edition, 2001. Assays for testing the further characteristics of neuronal differentiated cells are also known in the art.

The term "tumor cells which are able to differentiate into neuronal cells" as used herein means, for example, neuroblastoma cells, embryonic carcinoma cells, teratocarcinoma cells, neural hybrid cells (e.g. neuron×glioblastoma cells), or fibroblastoma cells. Examples of such tumor cells which are able to differentiate into neuronal cells include mouse and human tumor cells, i.e. P19 (murine embryonic carcinoma) cells, SiMa (human neuroblastoma) cells or SH-SY5Y (human neuroblastoma).

The term "neuroblastoma" as used herein means a cancer that develops from nerve cells found in several areas of the body. Neuroblastoma most commonly arises in and around the adrenal glands, which have similar origins to nerve cells and sit atop the kidneys. However, neuroblastoma can also develop in other areas of the abdomen and in the chest, neck and pelvis, where groups of nerve cells exist. The term "neuroblastoma cell" as used herein comprises one or more neuroblastoma cells which are neurotoxin-sensitive and capable of differentiating to neuronal cells. The neuroblastoma cell can be a primary neuroblastoma cell or a primary neuroblastoma cell line. Encompassed by said term are also established neuroblastoma cells or cell lines. The neuroblastoma cell can be a mammalian neuroblastoma cell, for example, a rodent neuroblastoma cell such as a rat or mouse neuroblastoma cell, but also a monkey neuroblastoma cell, such as a rhesus, macaque, or cynomolgus neuroblastoma cell or a primate neuroblastoma cell such as a chimpanzee neuroblastoma cell or, preferably, a human neuroblastoma cell. Examples of established neuroblastoma cell lines encompass, e.g., Neuro-2a (mouse neuroblastoma), Kelly (human neuroblastoma), SH-SY5Y (human neuroblastoma) or SiMa (human neuroblastoma). Human neuroblastoma cells are preferably used in the methods of the invention in order to generate neurotoxin-sensitive, neuronal differentiated cells. More preferably, the neuroblastoma cell as defined herein is a SiMa cell or SiMa cell line. This is because SiMa cells are easy to transfer, in a BoNT-sensitive form. In addition, they have high sensitivity to BoNT. Moreover, the differentiation protocol for SiMa cells is simple and rather short, in comparison to other neuroblastoma cells or cell lines. The SiMa cells as used in the method of the invention can be parental SiMa cells or (sub)clones derived therefrom.

The term "contacting" as used in accordance with the method of the invention refers to bringing the aforementioned neurotoxin-sensitive cells and the neurotoxin in physical proximity as to allow physical and/or chemical and/or biological interaction. The neurotoxin polypeptide can be a native, recombinant, isolated, modified, essentially purified or purified neurotoxin polypeptide or variant thereof. Alternatively, the neurotoxin can be comprised by a sample, preferably a biological sample such as a cell, cell lysate, blood, plasma, serum or lymph fluid. Suitable conditions which allow for specific interaction are well known to the skilled worker. Said conditions will depend on the cells and neurotoxins to be applied in the methods of the present invention, and can be adapted by the skilled artisan without further ado. Moreover, a time being sufficient to allow interaction can also be determined by the skilled worker by routine experimentation. For example, a specific amount of an isolated or recombinant neurotoxin polypeptide or a variant thereof as defined herein or a sample comprising a neurotoxin polypeptide can be added to the neurotoxin-sensitive cells. Thereafter, the cells are incubated with the neurotoxin polypeptide for at least 24 h, preferably 48 h, more preferably for 72 h under conditions which allow for the neurotoxin polypeptide to exert its biological activity. "Conditions which allow for the neurotoxin polypeptide to exert its biological activity" as used herein are known in the art.

The term "neurotoxin", "neurotoxin polypeptide" or "neurotoxin protein" as used in the present invention refers to the seven distinct serotypes of Botulinum neurotoxins, i.e. BoNT/A, BoNT/B, BoNT/C1, BoNT/D, BoNT/E, BoNT/F, BoNT/G, and to Tetanus Neurotoxin (TeNT), and variants thereof as defined herein. The corresponding nucleic acid and amino acid sequences are known in the art; see, e.g., Uniprot or TREMBL sequence database or WO 2010/124998, the disclosure content of which is incorporated herewith by reference. Preferably, BoNT/A, BoNT/C1 or BoNT/E is used in the methods of the invention. The corresponding receptors and substrates for said neurotoxins are well described in the art. The neurotoxin polypeptide can be a naturally occurring neurotoxin or a non-naturally occurring neurotoxin. A naturally occurring neurotoxin polypeptide is produced by a naturally occurring process, including, for example, isoforms produced from a post-translational modification, an alternatively-spliced transcript or a spontaneous mutation and subtypes. For instance, BoNT/A subtypes are BoNT/A1 subtype, BoNT/A2 subtype, BoNT/A3 subtype, BoNT/A4 subtype or BoNT/A5 subtype. A naturally occurring neurotoxin polypeptide includes the above-referenced sequences in which 1, 2, 3, 4, 5, 6, 7, 8, 9, 10, 20, 30, 40, 50, 100 or more amino acid residues are added, substituted or deleted. Commercially available pharmaceutical compositions which comprise a naturally-occurring BoNT/A have already been mentioned in the introductory part. A non-naturally occurring neurotoxin polypeptide means any neurotoxin polypeptide whose structure was modified with the aid of human manipulation, including, for example, a neurotoxin polypeptide with an altered amino acid sequence produced by genetic engineering using random mutagenesis or rational design and a neurotoxin polypeptide generated by chemical synthesis. Such non-naturally occurring neurotoxin polypeptides have been described in the art.

In another aspect of the invention, the neurotoxin polypeptide has an amino acid sequence being at least 40%, at least 50%, at least 60%, at least 70%, at least 75%, at least 80%, at least 85%, at least 90%, at least 95%, at least 98% or at least 99% identical to the amino acid sequence of BoNT/A, BoNT/B, BoNT/C1, BoNT/D, BoNT/E, BoNT/F, BoNT/G, or Tetanus neurotoxin, as defined herein. Envisaged are also the polynucleotides encoding the neurotoxin polypeptide, wherein the polynucleotides have a sequence being at least 40%, at least 50%, at least 60%, at least 70%, at least 75%, at least 80%, at least 85%, at least 90%, at least 95%, at least 98% or at least 99% identical to the polynucleotide sequence of BoNT/A, BoNT/B, BoNT/C1, BoNT/D, BoNT/E, BoNT/F, BoNT/G, or Tetanus neurotoxin, as defined herein. Identical as used in the present invention refers to sequence identity of polynucleotide or amino acid sequences wherein the sequences are aligned so that the highest order match is obtained. This can be achieved by using published techniques or methods codified in computer programs such as, for example, BLASTP, BLASTN, FASTA, Altschul 1990, J. Mol. Biol. 215, 403. The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (1987, J. Mol. Evolution 25, 351; Higgins 1989 CABIOS 5, 151) or the programs Gap and BestFit (Needleman and Wunsch 1970, J Mol Biol 48; 443; Smith and Waterman 1981, Adv. Appl. Math. 2, 482), which are part of the GCG software packet (Genetics Computer Group 1991, 575 Science Drive, Madison, Wis., USA 53711), are to be used. The sequence identity values recited above in percent (%) are to be determined, in one aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. It will be understood that the aforementioned variants shall, in an aspect of the invention, retain, at least one of the biological properties of neurotoxins and, in an aspect, all of the biological properties of a neurotoxin polypeptide recited herein. In a further aspect, the variants can be neurotoxins having improved or altered biological properties, e.g., they may recognize and cleave cleavage sites in the substrate which are improved for enzyme recognition and/or cleavage or may be improved for receptor binding or any other property specified above.

The neurotoxins referred to herein, in principle, comprise an N-terminal light chain and a C-terminal heavy chain. The neurotoxins are produced as single chain precursor molecules, referred to as "unprocessed neurotoxin polypeptides". As a result of the subsequent processing, "processed neurotoxin polypeptide" is obtained. The said processed neurotoxin polypeptide exhibits the biological properties characteristic for a neurotoxin, namely, (a) receptor binding, (b) internalization, (c) translocation across the endosomal membrane into the cytosol, and/or (d) endoproteolytic cleavage of proteins involved in synaptic vesicle membrane fusion. Therefore, the processed neurotoxin polypeptide is referred to as biologically active or mature neurotoxin polypeptide. The biological activity of the neurotoxin polypeptides, in an aspect, results from all of the aforementioned biological properties, as set forth elsewhere herein.

The term "permeabilization" as used herein means the process of making a plasma or cell membrane of a neurotoxin-sensitive cell permeable. One method of cell permeabilization involves the permeabilization of plasma or cell membranes of neurotoxin-sensitive cells by incubation with a hemolysin, for example, streptolysin O (Barry, E. et al., Biotechniques, 15, 1016 (1993); Graves, J. D. et al., Biochem. J., 265, 407-413 (1990); Sekiya K, Satoh R, Danbara H, Futaesaku Y. A ring-shaped structure with a crown formed by streptolysin O on the erythrocyte membrane. J Bacteriol. 1993 September; 175(18): 5953-61), perfringolysin O (Prepore to pore transition of a cholesterol-dependent cytolysin visualized by electron microscopy. Dang, T. X., Hotze, E. M., Rouiller, I., Tweten, R. K., Wilson-Kubalek, E. M. J. Struct. Biol. (2005)), pneumolysin (Tilley S J, Orlova E V, Gilbert R J, Andrew P W, Saibil H R (April 2005). "Structural basis of pore formation by the bacterial toxin pneumolysin". Cell 121 (2): 247-56), listeriolysin O (Vazquez-Boland J A, Kuhn M, Berche P, Chakraborty T, Dominguez-Bernal G, Goebel W, Gonzalez-Zorn B, Wehland J, Kreft J. Listeria pathogenesis and molecular virulence determinants. Clin Microbiol Rev. 2001 July; 14(3): 584-640), a bacterial hemolysin or a pore forming toxin from snakes or spiders. Many hemolysins are pore-forming toxins, i.e. they are able to produce pores on the cytoplasmic membrane of cells, thereby permeabilizing the cells. Methods and protocols of permeabilizing cells using hemolysins are known in the art and described, e.g., in the above-indicated publications. The neurotoxin-sensitive cells are permeabilized under conditions which allow the release of the reporter protein but not the release of the anchor protein from the permeabilized cells. As appreciated by those skilled in the art, the plasma or cell membrane remains intact, by using permeabilization by a hemolysin. Membrane-associated proteins or membrane proteins remain in place, and only soluble proteins can pass the cell membrane and can leave the interior of the cell. The non-cleaved fusion protein is associated with the cell membrane and remains there, after permeabilization. From the cleaved fusion protein, the part containing the measurable signal, i.e. the reporter protein, can leave the interior of the cell and is thereby physically separated from the cell.

The term "amount" as used herein encompasses the absolute amount of, e.g., a reporter protein or a neurotoxin polypeptide, the relative amount or the concentration of the said protein or polypeptide as well as any value or parameter which correlates thereto or can be derived there from.

The term "determining the amount" of, e.g., a reporter protein or neurotoxin polypeptide relates to measuring the absolute amount, relative amount or concentration of, e.g., the reporter protein or neurotoxin polypeptide, in a quantitative or semi-quantitative manner. Suitable measures for detection are well known to those skilled in the art. It will be understood that the determination of the amount of reporter protein or neurotoxin polypeptide, in an aspect, also requires calibration of the method by applying standard solutions with predefined amounts of reporter protein or neurotoxin polypeptide. It is well known to those skilled in the art how to carry out such a calibration; see also the following Example.

The "reporter protein" or "detection protein" (both terms are interchangeable) as referred to herein is in one aspect an enzyme such as luciferase, alkaline phosphatase, beta-galactosidase, and horseradish peroxidase. For example, luciferases belong into a class of enzymes capable of catalyzing a light-emitting reaction. Luciferases occur naturally as firefly or bacterial luciferases. The structure of luciferases and their subunits as well as nucleic acid sequences encoding them are well known in the art and described, e.g., in Chon 1985, J. Biol. Chem. 260(10): 6139-46 and Johnston 1986, J. Biol. Chem. 261(11): 4805-11. Luciferase activity can be determined by measuring the enzymatic conversion of a luciferase substrate. The latter one can be measured by detecting the intensity of the light emitted during the conversion reaction. Suitable systems and kits for measuring the light emission that occurs during the conversion reaction catalyzed by luciferases are well known in the art and commercially available (providers are, e.g., Takara Clontech, Thermo Scientific, and Promega; see also publications by, e.g., Gailey, P. C., Miller, E. J. & Griffin, G. D. (1997) Low-cost system for real-time monitoring of luciferase gene expression. BioTechniques 22: 528-534; Gould, S. J. & Subramani, S. (1988) Firefly luciferase as a tool in molecular and cell biology. Analyt. Biochem. 175:5-13 Fulton, R. & Van Ness, B. (1993) Luminescent reporter gene assays for luciferase and beta-galactosidase using a liquid scintillation counter. BioTechniques 14:762-763; Lemasters, J. J. & Hackenbrock, C. R. (1977) Kinetics of product inhibition during firefly luciferase luminescence. Biochemistry 16(3): 445-447; Nguyen, V. T., Morange, M. & Bensaude, O. (1988) Firefly luciferase luminescence assays using scintillation counters for quantitation in transfected mammalian cells. Analyt. Biochem. 171: 404-408; Seliger, H. H. & McElroy, W. D. (1960) Spectral emission and quantum yield of firefly bioluminescence. Arch. Biochem. Biophys. 88:136-141; Vieites, J. M., Navarro-Garcia, F., Perez-Diaz, R., Pla, J. & Nombela, C. (1994) Expression and in vivo determination of firefly luciferase as gene reporter in Saccharomyces cerevisiae. Yeast 10:1321-1327). The luminescence mediated by the luciferase in a redox reaction is equivalent to the amount of neurotoxin polypeptide in the sample. Thus, by quantifying the activity of the luciferase released from the cells, the biological activity of the neurotoxin can be determined. A standard curve with known neurotoxin polypeptide concentrations can be used as a reference in parallel. As a further reference, a protein measurement can be carried out in order to match the signal by luciferase to the cell number in the sample which may vary from case to case. This method is routine in the art and can be carried out in parallel to the activity assays of the invention described above. Another suitable enzyme which can be used as reporter protein is beta-galactosidase. Assays using this enzyme are also commercially available and described in the art (Thermo Scientifc, Life Technologies, Promega; Nielsen, D. A., Chou, J., MacKrell, A. J., Casadaban, M. J. and Steiner, D. F. (1983) Proc Natl Acad Sci USA 80(17): 5198-202). Alternatively, a fluorescent protein such as GFP, YFP, BFP or RFP can be utilized as reporter protein. Assays using said reporter proteins are known in the art. The term "quantifying the activity of the reporter protein" as used herein means measuring the reporter protein activity of the cleaved fusion protein of the invention remaining in the soluble supernatant after permeabilization of the neurotoxin-sensitive cells or the residual reporter protein activity of the non-cleaved fusion protein of the invention remaining in or at the neurotoxin-sensitive cells or the total reporter protein activity of the fusion protein of the invention. For the determination of the total activity of the reporter protein, the activity of the reporter protein in the permeabilized cells can be determined, or the activity of the total remaining reporter protein after removal of the supernatant can be measured. Alternatively, a standardization or normalization factor, such as GFP in the fusion protein choline transporter-GFP-SNAP-25-luciferase of the invention, can be measured representing the total initial amount of the fusion protein of the invention. By quantifying the activity of the reporter protein released from the cells, the biological activity of the neurotoxin polypeptide can be determined.

The term "determining the biological activity of a neurotoxin polypeptide" as used herein means measuring the biological activity of a neurotoxin protein, namely, (a) receptor binding, (b) internalization, (c) translocation across the endosomal membrane into the cytosol, and/or (d) endoproteolytic cleavage of proteins involved in synaptic vesicle membrane fusion. More specifically, the overall cellular mechanisms whereby a neurotoxin (e.g., BoNT/A) cleaves a neurotoxin substrate (e.g., SNAP-25) encompasses the binding of the neurotoxin to its corresponding receptor (e.g., binding of BoNT/A to BoNT/A receptor), the internalization of the neurotoxin/receptor complex, the translocation of the neurotoxin light chain from an intracellular vesicle into the cytoplasm and the proteolytic cleavage of the neurotoxin substrate. In vitro and in vivo assays for determining the biological activity of a neurotoxin polypeptide are well known in the art and have been mentioned elsewhere herein (see, e.g., Pellett et al., Withemarsh et al Toxicol. Sciences 126(2), 426-435 (2012), WO 2010/105234 A1).

As used herein, the singular forms "a", "an" and "the" include both singular and plural reference unless the context clearly dictates otherwise. By way of example, "a cell" refers to one or more than one cell.

As used herein, the term "about" when qualifying a value of a stated item, number, percentage, or term refers to a range of plus or minus 10 percent, 9 percent, 8 percent, 7 percent, 6 percent, 5 percent, 4 percent, 3 percent, 2 percent or 1 percent of the value of the stated item, number, percentage, or term. Preferred is a range of plus or minus 10 percent.

The term "essentially purified" as used herein means that a neurotoxin polypeptide is essentially free of other host cell polypeptides, i.e. it may contain impurities of 10%, 9%, 8%, 7%, 6%, 5%, 4%, 3%, 2% or 1% host cell polypeptide.

The terms "comprising", "comprises" and "comprised of" as used herein are synonyms with "including", "includes", "encompassing", "encompasses" or "containing", "contains", and are inclusive or open-ended and do not exclude additional, non-recited members, elements or method steps. Evidently, the term "comprising" encompasses the term "consisting of". More specifically, the term "comprise" as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase "consisting of" means that the composition (or device, or method) has the recited elements (or steps) and no more. In contrast, the term "comprises" can encompass also a method including further steps, e.g., steps d) and e), in addition to steps a), b) and c).

In case numerical ranges are used herein such as "compound X in a concentration between 0.1 and 0.5 micromolar", the range includes not only 0.1 and 0.5 micromolar, but also any numerical value in between 0.1 and 0.5 micromolar, for example, 0.2, 0.3 and 0.4 micromolar.

The term "in vitro" as used herein denotes outside, or external to, the animal or human body. The term "in vitro" as used herein should be understood to include "ex vivo". The term "ex vivo" typically refers to tissues or cells removed from an animal or human body and maintained or propagated outside the body, e.g., in a culture vessel. The term "in vivo" as used herein denotes inside, or internal to, the animal or human body.

In a specific aspect, the method of the invention comprises the steps of:
  (a) expressing a fusion protein comprising (i) an anchor protein, (ii) a reporter protein and (iii) a neurotoxin cleavage site intervening the anchor protein and the reporter protein, in neurotoxin-sensitive cells which are able to differentiate into neuronal cells;
  (b) differentiating the neurotoxin-sensitive cells of step (a) in a culture medium under conditions and for a time which differentiate said neurotoxin-sensitive cells into neuronal differentiated cells;
  (c) incubating the neuronal differentiated cells of step (b) with a neurotoxin and cultivating the cells under conditions which allow the neurotoxin to exert its biological activity;
  (d) permeabilizing the neuronal differentiated cells of step (c) under conditions which allow the release of the reporter protein but not the release of the anchor protein from the permeabilized neuronal differentiated cells; and
  (e) quantifying the activity of the reporter protein released from the cells of step (d), thereby determining the biological activity of the neurotoxin.

In this specific aspect, the neurotoxin-sensitive cells are able to differentiate into neuronal cells. Preferably, said neurotoxin-sensitive cells that are able to differentiate into neuronal cells are tumor cells. In some aspects of the method of the invention, said tumor cells which are able to differentiate into neuronal cells are SiMa cells available, e.g., from DSMZ (German collection of Microorganisms and Cell cultures) under the ACC deposit number: 164. The SiMa cell line DSMZ ACC 164 is also known as parental SiMa cell line. SiMa cells as used in the methods of the invention can be parental SiMa cells or (sub)clones thereof. Such subclones are also known in the art; see, e.g., WO 2010/105234, U.S. Pat. No. 8,476,068 B2 or Ester Fernández-Salas, Joanne Wang, Yanira Molina, Jeremy B. Nelson, Birgitte P. S. Jacky, K. Roger Aoki-PloSOne; 2012 7(11) e49516. In other aspects, the tumor cells which are able to differentiate into neuronal cells are P19 cells (Jones-Villeneuve E M, McBurney M W, Rogers K A, Kalnins V I. Retinoic acid induces embryonal carcinoma cells to differentiate into neurons and glial cells. J Cell Biol. 1982 August; 94(2): 253-62; Staines W A, Craig J, Reuhl K, McBurney M W. Retinoic acid treated P19 embryonal carcinoma cells differentiate into oligodendrocytes capable of myelination. Neuroscience. 1996 April; 71(3): 845-53) or SH-SY5Y cells (Encinas, Mario, et al. "Sequential Treatment of SH-SY5Y Cells with Retinoic Acid and Brain-Derived Neurotrophic Factor Gives Rise to Fully Differentiated, Neurotrophic Factor-Dependent, Human Neuron-Like Cells." Journal of neurochemistry 75.3 (2000): 991-1003). Further neurotoxin-sensitive cells are mentioned elsewhere herein. Said cells can be cultivated according to the protocol of the DMSZ. In other specific aspects of this method, the neurotoxin-sensitive cells able to differentiate into neuronal cells are or are derived from primary cells, stem cells or induced pluripotent stem cells. Protocols for differentiating said cells into neuronal cells are described in the art; see, e.g., the cited publications.

In a specific aspect of the method of the invention, the anchor protein is a transmembrane protein. Preferably, the transmembrane protein is selected from the group consisting of a choline transporter, H1-receptor (histamine H1 receptor), G protein-coupled receptor (GPCR) and SV2.

In a specific aspect of the method of the invention, the neurotoxin cleavage site is selected from the group consisting of a BoNT/A, BoNT/B, BoNT/C1, BoNT/D, BoNT/D, BoNT/E, BoNT/F, BoNT/G and TeNT cleavage site. It will be understood that the neurotoxin cleavage site comprised in the fusion protein of the invention shall be made available by the fusion protein to a neurotoxin polypeptide such that the neurotoxin protease can recognize, bind to and cleave the fusion protein of the invention in the neurotoxin-sensitive cells under suitable conditions. The skilled artisan is well aware of how a suitable arrangement within the fusion protein can be designed. Moreover, the fusion protein can be tested for cleavage by proteolytically active neurotoxin polypeptide in neurotoxin-sensitive cells as described in the accompanying example.

In another specific aspect of the method of the invention, the reporter protein is an enzyme selected from the group consisting of luciferase, alkaline phosphatase, beta-galactosidase, and horseradish peroxidase or a fluorescent protein selected from the group consisting of GFP, YFP, BFP and RFP.

In a further specific aspect of the method of the invention, a hemolysin is used for the permeabilization of the cells. The neurotoxin-sensitive cells are permeabilized under conditions which allow the release of the reporter protein but not the release of the anchor protein from the permeabilized neurotoxin-sensitive cells.

The hemolysin is preferably selected from the group consisting of streptolysin O, perfringolysin O, pneumolysin, a bacterial hemolysin and a pore forming toxin from snakes or spiders. The use of hemolysins in permeabilizing cells and protocols in this regard are well described in the art.

In a particular aspect of the method of the invention, the fusion protein comprises or consists of a fusion protein selected from the group consisting of choline transporter-GFP-SNAP-25-luciferase, H1-receptor-SNAP-25-HRP and H1-receptor-SNAP-25-luciferase. Moreover, encompassed is in an aspect a fusion protein comprising an amino acid sequence as shown in SEQ ID NO: 2 or 4, or an amino acid sequence having at least 60%, 70%, 75%, 80%, 85%, 90%, 95%, 96%, 97%, 98% or 99% sequence identity to SEQ ID NO: 2 or SEQ ID NO: 4. Means and methods for the determination of sequence identity between two sequences are mentioned elsewhere herein. The percent identity values are, in one aspect, calculated over the entire amino acid sequence of the reference sequence, i.e. SEQ ID NO: 2 or 4. The amino acid sequence shown in SEQ ID NO: 2 (choline transporter-GFP-SNAP-25-luciferase; CHT-GFP-SNAP-LUC) is encoded by the nucleic acid sequences depicted in SEQ ID NO: 1 and 5, the amino acid sequence shown in SEQ ID NO: 4 (H1-receptor-SNAP-25-luciferase; H1R-SNAP-LUC) is encoded by the nucleic acid sequence depicted in SEQ ID NO: 3. The corresponding sequences are shown in the sequence listing.

In a further aspect of the method of the invention, the quantification of the activity of the reporter protein comprises the standardization of the activity of the reporter protein.

In a specific aspect of the method of the invention, the standardization of the activity of the reporter protein is carried out by determining the residual reporter protein activity of the non-cleaved fusion protein remaining in or at the neurotoxin-sensitive cells or the total reporter protein activity of the fusion protein.

In addition, the invention pertains to a fusion protein comprising (i) an anchor protein, (ii) a reporter protein, and (iii) a neurotoxin cleavage site intervening the anchor protein and the reporter protein, for determining the biological activity of a neurotoxin, in neurotoxin-sensitive cells. Preferably, the neurotoxin-sensitive cells are able to differentiate to neuronal cells.

The definitions and embodiments with respect to the method of the invention apply mutatis mutandis to the fusion protein, polynucleotide, vector, host cell and kit of the invention.

In a specific aspect of the fusion protein of the invention, the anchor protein is selected from the group consisting of choline transporter (CHT), H1-receptor, GPCR and SV2; the reporter protein is an enzyme selected from the group consisting of luciferase, alkaline phosphatase, beta-galactosidase, and horseradish peroxidase (HRP) or a fluorescent protein selected from the group consisting of GFP, YFP, BFP and RFP; and the neurotoxin cleavage site is selected from the group consisting of a BoNT/A, BoNT/B, BoNT/C1, BoNT/D, BoNT/E, BoNT/F, BoNT/G and TeNT cleavage site. Further encompassed is any combination of the mentioned anchor protein, reporter protein and neurotoxin cleavage site, in the fusion protein of the invention. Preferably, the arrangement of the fusion protein of the invention is, from the N-terminus to the C-terminus, anchor protein-neurotoxin cleavage site-reporter protein. If a standardization factor is used, the arrangement of the fusion protein of the invention is preferably anchor protein-standardization factor-neurotoxin cleavage site-reporter protein, from the N-terminus to the C-terminus.

In a still further specific aspect of the fusion protein of the invention, the fusion protein comprises or consists of a fusion protein selected from the group consisting of choline transporter-GFP-SNAP-25-luciferase (with GFP as a standardization or normalization factor), H1-receptor-SNAP-25-luciferase and H1-receptor-SNAP-25-HRP. Moreover, encompassed is in an aspect a fusion protein comprising an amino acid sequence as shown in SEQ ID NO: 2 or 4, or an amino acid sequence having at least 60%, 70%, 75%, 80%, 85%, 90%, 95%, 96%, 97%, 98% or 99% sequence identity to SEQ ID NO: 2 or SEQ ID NO: 4. Means and methods for the determination of sequence identity between two sequences are indicated elsewhere herein. The percent identity values are, in one aspect, calculated over the entire amino acid sequence of the reference sequence, i.e. SEQ ID NO: 2 or 4. The amino acid sequence shown in SEQ ID NO: 2 (choline transporter-GFP-SNAP-25-luciferase; CHT-GFP-SNAP-LUC) is encoded by the nucleic acid sequences depicted in SEQ ID NO: 1 and 5, the amino acid sequence shown in SEQ ID NO: 4 (H1-receptor-SNAP-25-luciferase; H1R-SNAP-LUC) is encoded by the nucleic acid sequence depicted in SEQ ID NO: 3. The corresponding sequences are shown in the sequence listing.

The invention also pertains to a polynucleotide encoding the fusion protein of the invention.

The term "polynucleotide" or "nucleic acid (molecule)" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be, in an aspect, a linear or circular molecule. The polynucleotide sequence codes for the fusion protein of the invention. Moreover, in addition to the nucleic acid sequences encoding the fusion protein of the invention, a polynucleotide as used herein may comprise additional sequences required for proper transcription and/or translation such as 5' or 3' UTR sequences. The nucleic acid sequences encoding the fusion protein of the present invention can be derived from the amino acid sequences by a skilled artisan without further ado. In light of the degeneracy of the genetic code, optimized codons may be used in the nucleic acid sequences encoding the fusion protein of the present invention. Thereby, optimal expression in, e.g., a neurotoxin-sensitive cell can be achieved.

The invention also pertains to a vector comprising the polynucleotide of the invention. In an aspect, said vector is an expression vector.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination. The vector encompassing the polynucleotides of the present invention, in an aspect, further comprises selectable markers for propagation and/or selection in a host or host cell. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. Moreover, in an aspect of the invention, the polynucleotide is operatively linked to expression control sequences allowing expression in prokaryotic or eukaryotic host cells or isolated fractions thereof in the said vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in E. coli, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Other expression systems envisaged by the invention shall permit expression in insect cells, such as polyhedrin promoter based systems.

Moreover, inducible expression control sequences may be used in an expression vector encompassed by the present invention. Inducible expression systems and suitable expression control sequences are well known in the art. For example, the tetracycline-responsive regulatory system for transcriptional transactivation is described in Zhu Z, Zheng T, Lee C G, Homer R J, Elias J A: Tetracycline-controlled transcriptional regulation systems: advances and application in transgenic animal modeling. Semin. Cell Dev. Biol. 2002, 13:121-8; or Shockett P, Schatz D: Inducible gene expression using an autoregulatory, tetracycline-controlled system. Curr. Protoc. Mol. Biol. 2002, Chapter 16: Unit 16.14. Such inducible vectors may comprise tet or lac operator sequences or sequences inducible by heat shock or other environmental factors are described in the art. For example, two commonly used inducible expression systems are Tet-Off and Tet-On; see Bujard and Gossen, Proc. Natl. Acad. Sci. U.S.A. 89 (12): 5547-51. They consist of a fusion of the Tet repressor and a VP16 activation domain to create a transcriptional activator protein (transactivator) rather than a repressor. Gene expression is activated as a result of binding of the Tet-Off or Tet-On protein to tetracycline response elements (TREs) located within an inducible promoter. The difference relates to their respective response to doxycycline (Dox), a more stable tetracycline analogue: Tet-Off activates expression in the absence of Dox, whereas Tet-On activates in the presence of Dox. Suitable vectors are commercially available. For example, the Tet-On 3G vector set by Clontech can be used to create tightly regulated and highly responsive tetracycline (Tet)-inducible mammalian expression systems that are turned on by the addition of doxycycline to the culture medium. The pCMV-Tet3G vector expresses Tet-On 3G, a tetracycline-controlled transactivator that exhibits high activity in the presence of the inducer doxycycline, and exceptionally low activity in its absence. Tet-On 3G results from the fusion of amino acids 1-207 of a mutant Tet repressor (TetR) to 39 amino acids that form three minimal "F"-type transcriptional activation domains from the herpes simplex virus VP16 protein. Constitutive expression of Tet-On 3G is driven by the human cytomegalovirus immediate early promoter ($P_{CMV\,IE}$). Further, an EF1alpha version is available for cell lines in which the CMV promoter is silenced. For further detailed information see Clontech catalogue number 631163 and references cited therein. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3, pcDNA3.1 (Invitrogen) or pSPORT1 (Invitrogen) or baculovirus-derived vectors. Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989), (2001) N.Y. and Ausubel, Current Protocols in Molecular Biology, Green Publishing Associates and Wiley Interscience, N.Y. (1994).

The invention further pertains to a host cell comprising the polynucleotide, the vector or the fusion protein of the invention.

The term "host cell" as used herein encompasses prokaryotic and eukaryotic host cells, preferably isolated prokaryotic and eukaryotic host cells. Preferably, the host cell is a eukaryotic host cell. A eukaryotic host cell as used herein is a cell of an animal, preferably mammalian or human cell line suitable for production of the fusion protein of the invention. The polynucleotide or vector of the invention can be stably integrated into the genome of the host cell or transiently expressed by the host cell. A host cell as referred to herein, thus, encompasses in an aspect, yeast cells, mammalian cells, including human cells, plant cells or insect cells, either as primary cells or as cell lines. For example, the neurotoxin-sensitive cells referred to herein can be used as host cells.

The fusion protein of the invention can be manufactured by chemical synthesis or recombinant molecular biology techniques well known for the skilled artisan; see, e.g., Sambrook, Molecular Cloning: A Laboratory Manual, Cold Spring Harbor Laboratory, third edition, 2001. In an aspect, such a method of manufacturing the fusion protein of the invention comprises (a) culturing the host cell described elsewhere herein and (b) obtaining from the said host cell the fusion protein. In an aspect of this method, the fusion protein of the invention can be obtained by conventional purification techniques from a host cell lysate including affinity chromatography, ion exchange chromatography, size exclusion chromatography and/or preparative gel electrophoresis. It is envisaged by the scope of the invention that the fusion protein includes polypeptide preparations comprising the fusion protein of the invention and other proteins in addition.

Further, the invention pertains to a kit comprising the fusion protein, polynucleotide encoding the fusion protein, vector and/or host cell of the invention. The term "kit" as used herein refers to a collection of means comprising the mentioned components of the present invention which is provided in separate or common vials in a ready to use manner for carrying out the method of the present invention. In an aspect, the kit comprises additional means for carrying out the method of the present invention, in an aspect, calibration standard solutions comprising neurotoxin polypeptide and/or means for measuring the reporter protein activity (e.g. luciferase activity) such as detection agents for the reporter protein or substrates converted by said reporter protein. Furthermore, the kit comprises instructions for carrying out the method of the present invention. These instructions can be provided as a manual or can be in the form of an computer-implementable algorithm on a data storage medium which upon implementation is capable of governing one or more steps of the method of the invention. In an aspect, the kit is to be used for carrying out the method of the invention specified above.

Finally, the invention relates to the use of a fusion protein, polynucleotide encoding the fusion protein, vector and/or host cell of the invention, for determining the biological activity of a neurotoxin, in neurotoxin-sensitive cells.

The invention will now be illustrated by the following example which shall, however, not be construed as limiting the scope of the present invention.

EXAMPLE

The DNA molecule with the sequence shown in SEQ ID NO: 5 encoding the amino acid sequence shown in SEQ ID NO: 2 (choline transporter-GFP-SNAP-25-luciferase; CHT-GFP-SNAP-LUC) is synthesized de novo, then cloned into pcDNA 3.1 vector (Life Technologies). Further the plasmid (DNA vector with inserted construct) is amplified, extracted and purified. DNA synthesis, cloning, amplification and isolation are performed by GeneArt, Life technologies.

The plasmid is transfected into SH-SY5Y cells (ATCC CRL-2266) using Lipofectamine 2000 (Life Technologies). Cell culture and transfection are performed according to the provider's instructions.

After transfection of the plasmid, the cells are cultivated in the presence of Gentamicine in order to selectively grow plasmid containing cells. As soon as the culture reaches approx. 5 million cells, a single cell cloning is performed using the method of limited dilution. By this, approx. 400 clones are created and tested for adhesion quality, growth rates, plasmid expression rate and sensitivity for BoNT/A. The expression rate is determined by measuring the GFP fluorescence while the BoNT/A sensitivity is tested by the western blot SNAP-25 cleavage assay, according to Pellett S, Tepp W H, Clancy C M, Borodic G E, Johnson E A. FEBS Lett. 2007 Oct. 16; 581(25): 4803-8. From the clones showing good adhesion and growth rates and BoNT/A sensitivities comparable or better than SH-SY5Y parental cells, those with the highest GFP expression rates are selected and stored in cell banks.

For the BoNT/A reporter assay, the cells are seeded on 96-well plates followed by differentiation according to Rasetti-Escargueil et al. (Enhanced sensitivity to Botulinum type A neurotoxin of human neuroblastoma SH-SY5Y cells after differentiation into mature neuronal cells by C. Rasetti-Escargueil, C. B. Machado, R. Preneta-Blanc, R. A. Fleck, D. Sesardic The Botulinum J. (TBJ), Vol. 2, No. 1, 2011). The differentiated cells are incubated for 72 h with BoNT/A diluted in culture medium to final concentrations between 0.01 and 10 pM in logarithmic steps. After incubation, the cells are washed once with PBS (10 mM Sodium Phosphate, 0.9% NaCl, pH 7.4) and permeabilized with 50µl Streptolysin 0 solution (10 mM Sodium Phosphate, 0.9% NaCl, 10 mM Dithiothreitol, 50 U/mL Streptolysin O, pH 7.4). After 15 min incubation at 37° C., the supernatant of each well is transferred into a white 96-well plate and the luciferase activity is determined, according to the provider's instructions (Sigma Aldrich LUC1-1KT). The cells remaining on the culture plates are washed once with PBS and the GFP fluorescence is measured in a plate reader. For each single well the Luc/GFP ratio is calculated by dividing the measured signal values. The BoNT/A biological activity is calculated by comparing the dose-response-curve of the unknown sample with the respective curve of a reference standard e.g. by parallel line assay.

The invention claimed is:

1. A method for determining the biological activity of a neurotoxin, the method comprising the steps of:
   (a) expressing a fusion protein comprising (i) an anchor protein, (ii) a reporter protein and (iii) a neurotoxin cleavage site intervening the anchor protein and the reporter protein, in neurotoxin-sensitive cells;
   (b) incubating the neurotoxin-sensitive cells of (a) with a neurotoxin and cultivating the neurotoxin-sensitive cells under conditions which allow the neurotoxin to exert its biological activity;
   (c) permeabilizing the neurotoxin-sensitive cells of (b) under conditions which allow the release of the reporter protein but not the release of the anchor protein from the permeabilized neurotoxin-sensitive cells; and
   (d) quantifying the activity of the reporter protein released from the permeabilized neurotoxin-sensitive cells of (c),
   thereby determining the biological activity of the neurotoxin.

2. The method of claim 1, wherein the neurotoxin-sensitive cells are derived from tumor cell lines, primary cells, stem cells or induced pluripotent stem cells.

3. The method of claim 1, wherein the anchor protein is a membrane protein selected from the group consisting of a choline transporter, H1-receptor, G protein-coupled receptor (GPCR) and SV2.

4. The method of claim 1, wherein the neurotoxin cleavage site is selected from the group consisting of a BoNT/A, BoNT/B, BoNT/C1, BoNT/D, BoNT/E, BoNT/F, BoNT/G and TeNT cleavage site.

5. The method of claim 1, wherein the reporter protein is an enzyme selected from the group consisting of luciferase, alkaline phosphatase, beta-galactosidase, and horseradish peroxidase (HRP) or a fluorescent protein selected from the group consisting of GFP, YFP, BFP and RFP.

6. The method of claim 1, wherein a hemolysin is used for the permeabilization of the neurotoxin-sensitive cells.

7. The method of claim 6, wherein the hemolysin is selected from the group consisting of streptolysin O, perfringolysin O, pneumolysin, a bacterial hemolysin and a pore-forming toxin from snakes or spiders.

8. The method of claim 1, wherein the fusion protein comprises a fusion protein selected from choline transporter-GFP-SNAP-25-luciferase, H1-receptor-SNAP-25-luciferase and H1-receptor-SNAP-25-HRP.

9. The method of claim 1, wherein the quantification of the activity of the reporter protein comprises the standardization of the activity of the reporter protein.

10. The method of claim 9, wherein the standardization of the activity of the reporter protein is carried out by determining the residual reporter protein activity of the non-cleaved fusion protein remaining in or at the neurotoxin-sensitive cells or the total reporter protein activity of the fusion protein.

11. A fusion protein consisting of (i) an anchor protein, (ii) a reporter protein, and (iii) a neurotoxin cleavage site intervening the anchor protein and the reporter protein, for determining the biological activity of a neurotoxin, in neurotoxin-sensitive cells.

12. The fusion protein of claim 11, wherein the anchor protein is selected from the group consisting of choline transporter, H1-receptor, G protein-coupled receptor (GPCR) and SV2; the reporter protein is an enzyme selected from the group consisting of luciferase, alkaline phosphatase, beta-galactosidase and horseradish peroxidase or a fluorescent protein selected from the group consisting of GFP, YFP, BFP and REP; and the neurotoxin cleavage site is selected from the group consisting of a BoNT/A, BoNT/B, BoNT/C1, BoNT/D, BoNT/E, BoNT/F, BoNT/G and TeNT cleavage site.

13. The fusion protein of claim 11, wherein the fusion protein comprises a fusion protein selected from choline transporter-GFP-SNAP-25-luciferase, H1-receptor-SNAP-25-luciferase and H1-receptor-SNAP-25-HRP.

14. A kit comprising the fusion protein of claim 11.

* * * * *